United States Patent
Morris

(10) Patent No.: US 6,673,561 B1
(45) Date of Patent: Jan. 6, 2004

(54) DIAGNOSTIC TEST FOR THROMBOTIC OR THROMBOEMBOLIC DISEASE

(75) Inventor: Timothy A. Morris, San Diego, CA (US)

(73) Assignee: Regents of the University of California, Oakland, CA (US)

(*) Notice: Subject to any disclaimer, the term of this patent is extended or adjusted under 35 U.S.C. 154(b) by 0 days.

(21) Appl. No.: 09/609,275

(22) Filed: Jun. 30, 2000

Related U.S. Application Data

(60) Provisional application No. 60/141,734, filed on Jun. 30, 1999.

(51) Int. Cl.[7] .................. G01N 33/53; G01N 33/543; G01N 33/544; G01N 33/551; G01N 33/558

(52) U.S. Cl. .................. 435/7.92; 435/7.1; 435/7.93; 435/7.94; 435/7.95; 435/13; 436/501; 436/512; 436/514; 436/516; 436/518; 436/524; 436/528; 436/529; 436/530; 436/531; 436/534; 436/535; 436/548; 436/172; 436/811; 530/387.9; 530/388.25; 530/389.3; 530/391.1; 530/391.3

(58) Field of Search ................. 435/7.1, 7.4, 7.92, 435/7.93, 7.94, 7.95, 13, 69.6, 70.21, 452, 331, 337, 975; 436/512, 501, 518, 524, 528–531, 534, 535, 538, 548, 172, 811, 514, 516; 530/387.3, 387.9, 388.25, 389.3, 391.1, 391.3

(56) References Cited

U.S. PATENT DOCUMENTS

| | | | |
|---|---|---|---|
| 5,731,147 A | 3/1998 | Bard et al. ............... | 435/6 |
| 5,807,538 A | 9/1998 | Dean et al. ............... | 424/1.69 |
| 5,876,947 A | 3/1999 | Kudryk et al. ........... | 435/7.1 |
| 6,066,448 A | 5/2000 | Wohlstadter et al. ..... | 435/6 |
| 6,078,782 A | 6/2000 | Leland et al. ............ | 455/6 |

FOREIGN PATENT DOCUMENTS

| | | | |
|---|---|---|---|
| WO | 99/05176 | 2/1999 | ........... C07K/16/36 |

OTHER PUBLICATIONS

Urano et al., 1985. Fibrinogenolysis and fibrinolysis in normal volunteers and patients with thrombosis after infusion of urokinase. Thrombosis Research 39:145–155.*

Qureshi et al., 1979. In–vitro stability of human fibrino peptide B. Thromb. Haemostasis 42:1316–1323.*

Hui, K.Y., et al., "Monoclonal antibodies to a synthetic fibrin–like peptide bind to human fibrin but not fibrinogen", Science, vol. 222, XP002080953, 1130, (Sep. 1, 1983).

Kaizu, K., et al., "Role of Intrarenal Coagulation and Anticoagulant Therapy in the Progression of Diabetic Nephropathy", Japanese J. of Nephrology, vol. 35, No. 1, XP002154952, 35–42, (Jan. 1993). Abstract only.

Naim, J.O., et al., "The generation of antibody inmice to tuftsin a naturally occurring phagocytosis stimulating tetrapeptide", Immunological Investigations, vol. 20, No. 4, XP002154954, 351–364, (1991), Abstract only.

Owens, R.J., et al., "The genetic engineeringof Monoclonal antibodies", J. of Immunological Methods, vol. 168, XP002914829, 149–165, (1994).

Shibata, K., et al., "Intraglomerular Coagulation and Fibrinolysis in Human Primary Glomerular Diseases ", Japanese J. of Nephrology, vol. 33, No. 8, XP002154953, 719–729, (Aug. 1991). Abstract only.

(List continued on next page.)

Primary Examiner—Christopher L. Chin
Assistant Examiner—James L. Grun
(74) Attorney, Agent, or Firm—Schwegman, Lundberg, Woessner & Kluth, P.A.

(57) ABSTRACT

Thrombotic or thromboembolic disease is detected or monitored by determining the presence or amount B in a urine sample.

23 Claims, 4 Drawing Sheets

OTHER PUBLICATIONS

Wilner, G.D., et al., "Immunochemical analysis of Rabbit antihuman fibrinopeptide B antibodies", *Biochemistry*,vol. 18, No. 23, XP002914823, 5078–5082, (1979).

"Urokinase Pulmonary Embolism Trial, Phase 1 Results,", *JAMA*, 214(12), pp. 2163–2172, (1970).

Becker, D.M., et al., "D–Dimer Testing and Acute Venous Thromboembolism", *Arch. Intern. Med.*, 156, pp. 939–946, (1996).

Bell Jr, W., "Defibrinogenating Enzymes", *Drugs*, pp. 18–31, (1997).

Bilezikan, S.B., et al., "Radioimmunoassay of Human Fibrinopeptide Beta and Kinetics of Fibrinopeptide Cleavage by Different Enzymes", *The Journal of Clinical Investigation*, 56, pp. 438–445, (1975).

Bini, A., et al., "Degradation of Cross–Linked Fibrin by Matrix Metalloproteinase 3 (Stromelysin 1): Hydrolysis of the gamma Gly404–Ala 405 Peptide Bond", *Biochemistry*, 35, pp. 13056–13063, (1996).

Bini, A., et al., "Fibrin and its Derivatives in the Normal and Diseased Vessel Wall", *Annals New York Academy of Sciences*, 667, pp. 112–126, (1992).

Bini, A., et al., "Flow and Antibody Binding Properties of Hydrated Fibrins Prepared from Plasma, Platelet Rich Plasma and Whole Blood", *Thrombosis Research*, 76(2), pp. 145–156, (1994).

Bini, A., et al., "Identification and Distribution of Fibrinogen, Fibrin, and Fibrin(ogen) Degradation Products in Atherosclerosis", *Arteriosclerosis*, 9(1), pp. 109–121, (1989).

Bini, A., et al., "Immonuchemical Characterization of Fibrinogen, Fibrin I, and Fibrin II in Human Thrombi and Atherosclerotic Lesions", *Blood*, 69(4), pp. 1038–1045, (1987).

Bini, A., et al., "Immunohistochemical Charaterization of Fibrin (ogen)–Related Antigens in Human Tissues Using Monoclonal Antibodies", *Laboratory Investigation*, 60(6), pp. 814–821, (1989).

Bounameaux, H., et al., "Measurement of D–dimer in plasma as diagnostic aid in suspected pulmonary embolism", *The Lancet*, 337, pp. 196–200, (1991).

Bounameaux, H., et al., "Value of Liquid Crystal Contact Thermography and Plasma Level of D–Dimer for Screening of Deep Venous Thrombosis Following General Abdominal Surgery", *Thrombosis and Haemostasis*, 67, pp. 603–606, (1992).

Bovill, E., et al., "Performance Chacteristics of Fibrinogen Assays", *Arch. Pathol. Lab. Med.*, 117, pp. 58–66, (1993).

Brandt, J.T., et al., "Laboratory Monitoring of Heparin. Effect of Reagents and Instruments on the activated Partial Thromboplastin Time", *Amer. J. Clin. Pathol.*, 76, pp. 530–537, (1981).

Burrows, C.M., et al., "A New Plasma Assay To Detect Thrombosis Associated with Acute PE and DVT", *American Journal of Respiratory and Critical Care Medicine*, p. 1, (1999).

Campbell, A., *Monoclonal Anitbody and Immunosensor Technology*, 23, Elsevier Sciences Publishers, Amsterdam, pp. 3–6, 20–23, 42–4, (1991).

Carrie, D., et al., "A comparison of the antithrombotic effects of heparin and of low molecular weight heparins with increasing antifactor Xa/antifactor IIa ratio in the rabbit", *British Journal of Haematology*, 83, pp. 622–626, (1993).

Carrie, D., et al., "Effects of Heparin, Dermatan Sulfate and of their Association on the Inhibition of Venous Thrombosis Growth in the Rabbit", *Thrombosis and Haemostatis*, 68, pp. 637–641, (1992).

Chung, D.W., et al., "Characterization of Complementary Deoxyribonucleic Acid and Genomic Deoxyribonucleic Acid for the Beta Chain of Human Fibrinogen", *Biochemistry*, 22, pp. 3244–3250, (1983).

Collen, D., et al., "Basic and Clinical Aspects of Fibrinolysis and Thrombolysis", *Blood*, 78(12), pp. 3114–3124, (1991).

Dalen, J.E., "American College of Chest Physicians and the National Heart, Lung and Blood Institute National Conference on Antithrombotic Therapy", *Arch. Intern. Med.*, 146, pp. 462–472, (1986).

Douketis, J.D., et al., "Risk of Fatal Pulmonary Embolism in Patients with Treated Venous Thromboembolism", *JAMA*, 279, pp. 458–462, (1998).

Dyr, J.E., et al., "Conversion of fibrinogen to fibrin induced by preferential release of fibrinopeptide beta", *Biochemica et Biophysica Acta*, 990, pp. 18–24, (1989).

Ebert, R.F., et al., "Assay of Human Fibrinopeptides by High–Performance Liquid Chromatography", *Analytical Biochemistry*, 148, pp. 70–78, (1985).

Eckhardt, T., et al., "Measurement of Desarginine Fibrinopeptide B in Human Blood", *J.Clin. Invest.*, 67, pp. 809–816, (Mar. 1981).

Fu, Y., et al., "Carboxyl–Terminal–Extended Variant of the Human Fibrinogen alpha Subunit: A Novel Exon Conferring Marked Homology to beta and gamma Subunits", *Biochemistry*, 31, pp. 11968–11972, (1992).

Fu, Y., et al., "Fib420: A normal human variant of fibrinogen with two extended alpha chains", *Proc. Natl. Acad. Sci. USA*, 91, pp. 2625–2628, (Mar. 1994).

Gando, S., et al., "Diagnostic and Prognostic Value of Fibrinopeptides in Patients with Clinically Suspected Pulmonary Embolism", *Thrombosis Research*, 75(2), pp. 195–202, (1994).

Gawoski, J.M., et al., "The Effects of Heparin on the Activated Partial Thromboplastin Time of the College of American Pathologists Survey Specimens", *Arch. Pathol. Lab Med*, 111, pp. 785–790, (Sep. 1987).

Ginsberg, J.S., et al., "Application of Novel and Rapid Whole Blood Assay for D–Dimer in Patients with Clinically Suspected Pulmonary Embolism", *Thromb Haemost*, 73, pp. 35–38, (1995).

Ginsberg, J.S., et al., "D–Dimer in Patients with Clinically Suspected Pulmonary Embolism", *Chest*, 104, pp. 1679–1684, (1993).

Goldhaber, S.Z., et al., "Quantitative Plasma D–dimer Levels Among Patients Undergoing Pulmonary Angiography for Suspected Pulmonary Embolism", *JAMA* 270, pp. 2819–2822, (1993).

Goldhaber, S.Z., et al., "Risk Factors for Pulmonary Embolism, The Framingham Study", *The American Journal of Medicine*,74, pp. 1023–1028, (1983).

Harlow, E., et al., *Antibodies: A Laboratory Manual*, Cold Springs Harbor Laboratory, pp. 72–77, 600–612, (1988).

Higgins, D.L., et al., "Steady State Kinetic Parameters for the Thrombin–catalyzed Conversion of Human Fibrinogen to Fibrin", *The Journal of Biological Chemistry*, 258, pp. 9276–9282, (1983).

Hirsch, D.R., et al., "Prevalence of Deep Venous Thrombosis Among Patients in Medical Intensive Care", *JAMA*,274, pp. 335–337, (1995).

Hirsch, D.R., et al., "Shortened hospitalization by means of adjusted–dose subcutaneous heparin for deep venous thrombosis", *Am. Heart J.*, 131, pp. 276–280, (1996).

Hoellerich, V.L., et al., "Diagnosing Pulmonary Embolism Using Clinical Findings", *Arch. Intern. Med.*, 146, pp. 1699–1704, (1986).

Hull, R., et al., "Continuous Intravenous Heparin Compared with Intermittent Subcutaneous Heparin in the Initial Treatment of Proximal–Vein Thrombosis", *The New England Journal of Medicine*, 315, pp. 1109–1114, (1986).

Hull, R.D., et al., "Subcutaneous Low–Molecular–Weight Heparin Compared with Continous Intravenous Heparin in the Treatment of Proximal–Vein Thrombosis", *The New England Journal of Medicine*, 326(15), pp. 975–982, (1992).

Hull, R.D., et al., "The Importance of Initial Heparin Treatment on Long–term Clinical Outcomes of Antithrombotic Therapy", *Arch. Intern. Med.*, 157, pp. 2317–2321, (1997).

Kinjoh, K., et al., "Production of a Monoclonal Antibody Against Rabbit Fibrinopeptide B(FPB) for Immunological Assay of Rabbit FPB", *Japanese Journal of Physiology*, 44, Abstract 272, p. S 117, (1994).

Koopman, J., et al., "Fibrinogen Marburg: A Homozygous Case of Dysfibrinogenemia, Lacking Amino Acids A alpha 461–610 (Lys 461 AAA Stop TAA)", *Blood*, 80, pp. 1972–1979, (1992).

Koopman, M., et al., "Treatment of Venous Thrombosis with Intravenous Unfractionated Heparin Administered in the Hospital as Compared with Subcutaneous Low–Molecular–Weight Heparin Administered at Home", *The New England Journal of Medicine*, 334, pp. 682–687, (1996).

Kudryk, B., et al., "A Monoclonal Antibody with Ability to Distinguish between NH2–Terminal Fragments Derived from Fibrinogen and Fibrin", *Molecular Immunology*, 20, pp. 1191–1200, (1983).

Kudryk, B., et al., "Cross–linking of fibrinogen by tissue transglutaminase: Involvement of the C–termini of the Aalpha–and gamma–chains in formation of A alpha gamma— dyads", *Thromb. Haemostas*, 69(6), Abstract No. 2560, p. 1260, (1993).

Kudryk, B., et al., "Measurement in Human Blood of Fibrinogen/Fibrin Fragments Containing the Bbeta 15–42 Sequence", *Thrombosis Research*, 25, pp. 277–291, (1982).

Kudryk, B., et al., "Modulation of Epitope Expression at C–Terminus Fibrinogen gamma Chain", *Thrombosis and Haemostas*, 65, Abstract 714, pp. 898, (1991).

Kudryk, B., et al., "Specificity of a Monoclonal Antibody for the NH2–Terminal Region of Fibrin", *Molecular Immunology*, 21, pp. 89–94, (1984).

Kudryk, B., et al., "Use of a Synthetic Homologue of Human Fibrinopeptide A for Production of a Monoclonal Antibody Specific for the Free Peptide", *Blood*, 74, pp. 1036–1044, (1989).

Kudryk, B.J., et al., "Monoclonal Antibodies as Probes for Fibrin(ogen) Proteolysis", *Monoclonal Anitbodies in Immunoscintigraphy*, CRC Press, Inc. Florida, pp. 365–398, (1989).

Levine, M., et al., "A Comparison of Low–Molecular–Weight Heparin Administered Primarily at Home with Unfractionated Heparin administered in the Hospital for Proximal Deep–Vein Thrombosis", *The New England Journal of Medicine*, 334, pp. 677–681, (1996).

Loike, J.D., et al., "CD11c/CD18 on neutrophils recognizes a domain at the N terminus of the Aalpha chain of fibrinogen", *Proc. Natl. Acad. Sci. USA*, 88, pp. 1044–1048, (1991).

Lopaciuk, S., et al., "Subcutaneous Low Molecular Weight Heparin versus Subcutaneous Unfractionated Heparin in the Treatment of Deep Vein Thrombosis: a Polish Multicenter Trial", *Thrombosis and Haemostasis*, 68(1), pp. 14–18, (1992).

Lui, C.Y., et al., "Immunologic Identification of the Cleavage Products from the Aalpha–and Bbeta–Chains in the Early Stages of Plasmin Digestion of Fibrinogen", *Thrombosis and Haemostasis*, 56(1), pp. 100–106, (1986).

Marsh, J.J., et al., "Supression of Thrombolysis in a Canine Model of Pulmonary Embolism", *Circulation*, 90, pp. 3091–3097, (1994).

Meyer, G., et al., "Subcantaneous Low–Molecular–Weight Heparin Fragmin Versus Intravenous Unfractionated Heparin in the Treatment of Acute Non Massive Pulomonary Embolism: An Open Randomized Pilot Study", *Thrombosis and Haemostatis*,74, pp. 1432–1435, (1995).

Miller, G.J., et al., "The Effects of Quality and Timing of Venepuncture on Markers of Blood Coagulation in Healthy Middle–aged Men", *Thrombosis and Haemostatis*,73, pp. 82–86, (1995).

Morris, T., et al., "Anti–fibrin Monoclonal Antibodies Detect Deep Vein Thrombosis in a Canine Model", *Chest*, 104, Abstract, p. 24S, (1993).

Morris, T., et al., "Anti–thrombotic Efficacies of Enoxaparin, Dalteparin, and Unfractioned Heparin in Venous Thrombi–embolism", *Thrombosis Research*, 100, pp. 185–194, (2000).

Morris, T.A., et al., "Antibodies Against the Fibrin Beta–Chain Amino–Terminus Detect Active Canine Venous Thrombi", *Circulation*, 96(9), pp. 3173–3179, (1997).

Morris, T.A., et al., "Degree of Polymer Organization Decreases the Binding of a Monoclonal Antibody Raised against the Beta–Chain Amino Terminus of Fibrin", *Thrombosis and Haemmostasis*, 77, pp. 704–709, (1997).

Moser, K.M., et al., "Study of Factors that May Condition Scintigraphic Detection of Venous Thrombi and Pulmonary Emboli with Indium–111–Labeled Platelets",*The Journal of Nuclear Medicine*, 21(11), pp. 1051–1058, (1980).

Ng, A.S., et al., "(20) Quantifying Thrombin–Catalyzed Release of Fibrinopeptides from Fibrinogen Using High–Performance Liquid Chromatography", *Methods in Enzymology*, 222, pp. 341–358, (1993).

Plow, E.F., et al., "Surface Markers of Fibrinogen and Its Physiologic Derivatives Revealed by antibody Probes", *Seminars in Thrombosis and Hemostasis*, 8(1), pp. 36–56, (1982).

Procyk, R., et al., "Accessibility of Epitopes on Fibrin Clots and Fibrinogen Gels", *Blood*, 77(7), pp. 1469–1475, (1991).

Raschke, R.A., et al., "The Weight–based Heaprin Dosing Nomogram Compared with a "Standard Care" Nomogram", *Ann. Intern. Med.*,119, pp. 874–881, (1993).

Reber, G., et al., "A new, semi–quantitative and individual ELISA for rapid measurment of plasma d–dimer in patients suspected of pulmonary embolism", *Blood Coagulation and Fibrinolysis*, 6, pp. 460–463, (1995).

Singer, I., et al., "VDIPEN, A Metalloproteinase–generated Neoepitope, Is Induced and Immunolocalized in Articular Cartilage during Inflammatory Arthritis", *Journal of Clinical Investigation*, pp. 2178–2186, (1995).

Southan, C., et al., "Direct analysis of plasma fibrinogen–derived fibrinopeptides by high–performance liquid chromatography: investigation of nine congenital fibrinogen abnormalities", British Journal of Haemtology, 65, pp. 469–473, (1987).

Southan, E., et al., "Direct Analysis of Plasma Fibrinogen–Derived Fibrinopeptides by High–Performance Liquid Chromatography", Thrombosis Research, 43, pp. 195–204, (1986).

Tapson, V.F., et al., "American Thoracic Society Position Paper: The Diagnostic Approach to Acute Venous Thromboembolism", American Journal of Respiratory and Critical Care Medicine, 160, pp. 1044–1066, (1999).

Valenzuela, R., et al., "Immunoelectrophoretic and Immunohistochemical Characterizations of Fibrinogen Derivatives in Atherosclerotic Aortic Intimas and Vascular Prosthesis Pseudo–intimas", American Journal of Pathology, 141, pp. 861–880, (1992).

van Beek, E., et al., "The role of plasma D–dimer concentration in the exclusion of pulmonary embolism", British Journal of Haematology, 92, pp. 725–732, (1996).

van den Besselaar, A., et al., "Monitoring Heparin Therapy; Relationships between the Activated Partial Thromboplastin Time and Heparin Assays Based on Ex–Vivo Heparin Samples", Thrombosis and Haemmostasis, 63, pp. 16–23, (1990).

van Hulsteijn, H., et al., "Diagnostic Value of Fibrinopeptide A and Beta–Thromboglobulin in Acute Deep Venous Thrombosis and Pulmonary Embolism", Acta. Med. Scand., 211, pp. 323–330, (1982).

Verstraete, M., "Direct Thrombin Inhibitors: Appraisal of the Antithromboptic/Hemorrhagic Balance", Thrombosis and Haemostasis, 78, pp. 357–363, (1997).

Walenga, J., et al., "Biochemical and Pharmacologic Rationale for the Development of a Synthetic Heparin Pentasaccharide", Thrombosis Research, 86, pp. 1–36, (1997).

Weissbach, L., et al., "Bipartite mRNA for chicken alpha–fibrinogen potentially encodes an amino acid sequence homologous to beta– and gamma–fibrinogens", Proc. Natl. Acad. Sci., USA, 87, pp. 5198–5202, (1990).

Yung, G.L., et al., "Fibrinopeptide A Levels in Primary Pulmonary Hypertension", American Journal of Respiratory and Critical Care Medicine, 157, Abstract, pp. A592, (1998).

* cited by examiner

DIAGNOSTIC TEST FOR THROMBOTIC OR THROMBOEMBOLIC DISEASE

This application claims the benefit of U.S. Provisional Application No. 60/141,734, filed Jun. 30, 1999.

BACKGROUND OF THE INVENTION

The invention is designed to improve the medical care of patients with thrombotic or thromboembolic disease, such as deep venous thrombosis (DVT) and pulmonary embolism (PE), by facilitating clinical diagnosis and by providing a means by which the effectiveness of treatment can be measured.

The most challenging aspect of caring for patients with DVT and PE concerns making the initial diagnoses. In fact, most PE fatalities occur before the disease has been detected. Clinical signs and symptoms are neither sensitive nor specific; and the subsequent evaluative process for diagnosing DVT and/or PE is time consuming, expensive, and potentially invasive. The non-invasive diagnostic techniques for these diseases focus on demonstrating defects in the vascular anatomy, findings that are not specific for active thrombosis. For example, compression ultrasonography (CUS) can be used to detect pathology in the femoral vein. However, the distinction between a new thrombus and focal wall thickening from a previous thrombus cannot be made reliably. In addition CUS cannot be used to reliably detect asymptomatic DVT. As a result, attention has been focused on the identification of a serologic marker that would indicate active thrombosis.

In the last decade, the utility of plasma D-Dimer levels for identifying thromboembolic disease has been investigated extensively. D-Dimers are formed as a result of the degradation of cross-linked fibrin, and plasma levels have been shown to be elevated in both DVT and PE. However, plasma D-Dimer levels reflect the rate of fibrinolytic activity, but not necessarily the rate of fibrin formation. As a result, plasma D-Dimer levels are elevated in a variety of pathologic conditions involving previous fibrin formation, such as sepsis, DIC, pneumonia, and malignancy. In fact, only 22% of medical inpatients (presumably without thomboembolic disease) do not have elevated D-Dimer levels.

Although anticoagulants have been used for decades to treat thromboembolic disease, venous thromboembolism (VTE) in particular, the ideal method of treating this disease is unresolved. It is generally accepted that early anticoagulation dramatically reduces short-term mortality (Douketis et al. 1998), and it is becoming apparent that the incidence of long-term sequelae such as recurrent DVT and PE are also dependant upon the intensity of treatment in the first few days after diagnosis (Hull et al. 1997). The optimal method of early anticoagulation for VTE is, however, a controversial issue. New anti-thrombotic strategies are constantly in development, including improved dosing regimens for unfractionated heparin (Raschke et al. 1993, Lopaciuk et al. 1992, Hirsch et al. 1996), low molecular weight heparins (Levine et al. 1996, Koopman et al. 1996m Meyer et al. 1995) and specific inhibitors of the coagulation enzymes thrombin (Verstraete 1997) and factor Xa (Walenga et al. 1997). Each regimen has a specific anti-thrombotic potency, defined as its ability to suppress in situ thrombus propagation. It is likely that the benefits of these newer anticoagulant strategies will depend on the relationship between early anti-thrombotic effects and long-term clinical outcomes.

Although anticoagulants may have different mechanisms of action, the ultimate biochemical goal is the same, to prevent thrombin-mediated conversion of fibrinogen to fibrin and thus stop thrombus propagation (anti-thrombosis). Unfortunately, the anticoagulant potencies of these medications, measured by in vitro tests of activity such as the activated partial thromboplastin time (aPTT) and the plasma anti-Xa activity, do not reliably predict their anti-thrombotic effects in animal models (Carrier et al. 1993), Carrier et al. 1992, Morris et al. 1998).

There is growing recognition that inadequate initial treatment of VTE predisposes to fatal pulmonary emboli (Dalen 1986) and long-term recurrence (Hull 1997). However, there are limitations to the data suggesting that low antithrombotic activity itself in the early treatment of VTE leads to poor clinical outcomes. For example, anticoagulant activities of patients receiving unfractionated heparin are generally measured using the plasma aPTT, which has only a moderate correlation with actual plasma heparin levels (Gawoski et al. 1987, Brandt et al. 1981, van den Besselaar et al. 1990)). Furthermore, even the moderate correlation between anticoagulant activity and anti-thrombotic effect observed in animal models of thrombosis has not been validated in humans. Finally, the assumption that the intensity of anti-thrombosis correlates with the clinical efficacy, though reasonable, has not been tested in humans. For example, there have been no clinical studies to correlate VTE recurrence with the anti-thrombotic effects of anticoagulation.

Measuring the anti-thrombotic effects of anticoagulants in humans with VTE is difficult. The most commonly used non-invasive tests for diagnosis of DVT (compression ultrasonography, impedance plethysmography and magnetic resonance imaging) and PE (ventilation-perfusion scanning and helical CT scanning) do not provide sufficient anatomical information to determine reliably whether thromboemboli have enlarged acutely. Invasive studies such as contrast venography and angiography, while better at demonstrating gross changes in thrombus size (Lopaciuk et al. 1992, National Heart 1970) can be painful and are often impractical for following treatment. Furthermore, they may not be able to detect subtle increases in clot dimensions due to ongoing thrombosis. Finally, all of the anatomical tests described above share the limitation of being unable to differentiate the effects of anticoagulation (preventing clot enlargement) from the effects of the intrinsic fibrinolytic system (reducing clot size).

The most commonly used serological test for VTE, the D-dimer test, is also unsuitable as a marker of acute thrombosis. Although increasingly recognized as a sensitive indicator of VTE, the test measures thrombolytic fragments from pre-existing clots, and would not correlate with thrombus propagation. Likewise, serum markers of thrombin activation, such as prothrombin F1+2 fragments and thrombin-antithrombin III complexes, are not direct indicators of fibrin(ogen) conversion and polymerization. Thus anticoagulants with different spectra of activity against factor Xa and thrombin (for example heparin pentasaccharide and hirudin) would be expected to affect these tests differently, even if their in vivo and anti-thrombotic effects were the same.

Therefore, an ongoing need exists for a reliable test for DVT and PE, and also for a test to determine the effectiveness of different therapeutic regimens. Also the discovery of a marker with sufficient specificity and sensitivity in detecting PE and/or DVT would aid in diagnostic accuracy, and facilitate cost-effective utilization of resources. Thus, only those patients with a positive test would require anticoagulation and further evaluation with the appropriate tests.

SUMMARY OF THE INVENTION

The present invention provides a method for detecting thrombotic or thromboembolic disease, such as PE and/or DVT, by measuring the levels of fibrinopeptide B (FPB) in a physiological sample. The sample may be blood, plasma or, preferably, urine. The present invention also provides methods for monitoring the treatment of thrombotic or thromboembolic disease in a patient by monitoring changes in the levels of FPB in blood, plasma or, preferably, urine. The present invention also provides assay methods for conducting these measurements. The invention also provides peptides that include sequences from FPB; these peptides may be used as calibrators or controls in assays for FPB, they may be linked to carrier proteins and used to generate antibodies against FPB and/or they may be linked to labels or solid phases and used as competitors in competitive assays for FPB. The invention also provides reagents, compositions, and kits for carrying out immunoassays for FPB.

The present invention provides a fibronopeptide B (FPB) peptide defined by an amino acid sequence indicated in SEQ ID NO:1, and an FPB peptide defined by an amino acid sequence indicated in SEQ ID NO:2. These peptides may be covalently linked to a carrier molecule, such as keyhole limpet hemocyanin (KLH). Also these peptides and derivatives thereof may be attached to a substrate, such as a gel, hydrogel, resin, bead, magnetic bead, electrode, nitrocellulose, nylon filter, microtiter plate, culture flask, or polymeric material. The peptide may have a detectable moiety operably linked to it, and the detectable moiety may be a radionuclide, enzyme, specific binding pair component, colloidal dye substance, fluorochrome, reducing substance, latex, digoxigenin, metal, particulate, dansyl lysine, antibody, protein A, protein G, electron dense material, chemiluminescent substance, electrochemiluminescent substance, electroactive compound or chromophore.

The present invention also provides an antibody or fragment thereof that specifically recognizes an FPB peptide defined by an amino acid sequence indicated in SEQ ID NO:1, SEQ ID NO:2, SEQ ID NO:3, SEQ ID NO:4, SEQ ID NO:5 or SEQ ID NO:6. Such a fragment may be an Fab, F(ab')$_2$, or Fv fragment. The antibody or fragment thereof may be attached to a substrate, such as a gel, hydrogel, resin, bead, magnetic bead, electrode, nitrocellulose, nylon filter, microtiter plate, culture flask, or polymeric material. The antibody or fragment thereof may have a detectable moiety operably linked to it, and the detectable moiety may be a radionuclide, enzyme, specific binding pair component, colloidal dye substance, fluorochrome, reducing substance, latex, digoxigenin, metal, particulate, dansyl lysine, antibody, protein A, protein G, electron dense material, electrochemiluminescent substance, chemiluminescent substance or chromophore.

The present invention further provides a continuous cell line that produces an antibody that specifically recognizes a target peptide, wherein the target peptide is an FPB peptide defined by an amino acid sequence indicated in SEQ ID NO:1, SEQ ID NO:2, SEQ ID NO:3, SEQ ID NO:4, SEQ ID NO:5 or SEQ ID NO:6. The cell line may be a monoclonal antibody cell line.

The present invention further provides an animal that produces polyclonal antibodies that specifically recognizes a target peptide, wherein the target peptide is an FPB peptide defined by an amino acid sequence indicated in SEQ ID NO:1, SEQ ID NO:2, SEQ ID NO:3, SEQ ID NO:4, SEQ ID NO:5 or SEQ ID NO:6. The target peptide may be covalently linked to a carrier molecule. It may be keyhole limpet hemocyanin (KLH).

The present invention provides diagnostic method for detecting thrombotic or thromboembolic disease in a patient having the step of detecting the presence or amount of FPB in a sample such as a physiological fluid taken from the patient, to determine whether the patient has thrombotic or thromboembolic disease. The thrombotic or thromboembolic disease to be detected may be deep venous thrombosis (DVT) or pulmonary embolism (PE). The physiological fluid to be tested may be a fluid, such as blood or urine. Examples of techniques that can be used for the detection step include mass spectrometry, peptide sequencing, chromatography (e.g., HPLC or TLC), electrophoresis (e.g., capillary electrophoresis), enzyme-linked immunosorbent assay, immunonephelometry, agglutination, precipitation, immunodiffusion, immunoelectrophoresis, electrochemiluminescent immunoassay, electrochemical immunoassay, chemiluminescent immunoassay, western blot, immunofluorescence, radioimmunoassay, and immunohistochemistry. The amount of FPB present in the sample is considered "positive" for thrombotic or thromboembolic disease if it is significantly above the normal range or if it is in a range that is indicative of thrombotic or thromboembolic disease. The exact cutoff values used will vary depending on the desired assay sensitivity and selectivity. In one embodiment, the amount of FPB present in a blood or plasma sample is considered "positive" for thrombotic or thromboembolic disease if it is above 5 ng/ml, and in particular if it is above 10 ng/ml. In an alternative embodiment, the amount of FPB present in a urine sample is considered "positive" for thrombotic or thromboembolic disease if it is above 50 ng/ml, and in particular if it is above 100 ng/ml.

The present invention provides diagnostic method for detecting thrombotic or thromboembolic disease in a patient having the steps of contacting a physiological sample suspected of containing fibrinopeptide B (FPB) and des-arginine FPB with an amount of detection agent specific for FPB to form an FPB:detection agent complex; wherein the detection agent is an antibody or fragment thereof that specifically recognizes an FPB peptide defined by an amino acid sequence indicated in SEQ ID NO:1, SEQ ID NO:2, SEQ ID NO:3, SEQ ID NO:4, SEQ ID NO:5 or SEQ ID NO:6; and detecting the presence or amount of FPB:detection agent complex present in the sample to determine whether the patient has thrombotic or thromboembolic disease. The method may include a step of removing fibrinogen from the physiological sample. The thrombotic or thromboembolic disease to be detected may be deep venous thrombosis (DVT) or pulmonary embolism (PE). The physiological fluid to be tested may be a fluid, such as blood, plasma or urine. The detection step may be by enzyme-linked immunosorbent assay, immunonephelometry, agglutination, precipitation, immunodiffusion, immunoelectrophoresis, electrochemiluminescent immunoassay, chemiluminescent immunoassay, electrochemical immunoassay, western blot, immunofluorescence, radioimmunoassay, or immunohistochemistry. The amount of FPB:detection agent complex present in the plasma sample is considered "positive" for thrombotic or thromboembolic disease if it is above 5 ng/ml, and in particular if it is above 10 ng/ml. The amount of FPB:detection agent complex present in the urine sample is considered "positive" for thrombotic or thromboembolic disease if it is above 50 ng/ml, and in particular if it is above 100 ng/ml.

The present invention provides a method for monitoring the treatment of thrombotic or thromboembolic disease in a patient by monitoring changes in the levels of FPB in physiological samples such as blood, plasma, or ,preferably, urine. The monitoring may comprise the steps of contacting a physiological sample suspected of containing fibrinopeptide B (FPB) and des-arginine with an amount of detection agent specific for FPB to form an FPB:detection agent complex, wherein the detection agent is an antibody or fragment thereof that specifically recognizes an FPB peptide defined by an amino acid sequence indicated in SEQ ID NO:1, SEQ ID NO:2, SEQ ID NO:3, SEQ ID NO:4, SEQ ID NO:5 or SEQ ID NO:6; detecting the amount of FPB:detection agent complex present in the sample; repeating the steps at a point later in time; and comparing the amounts determined at the two time points and correlating the change in the amounts to determine whether the thrombosis or embolism is diminishing in size. The method may include a step of removing fibrinogen from the sample.

The present invention also provides a diagnostic method for detecting thrombotic or thromboembolic disease in a patient involving contacting a urine sample suspected of containing fibrinopeptide B (FPB) and des-arginine FPB with an amount of detection agent specific for FPB to form an FPB:detection agent complex, wherein the detection agent is an antibody or fragment thereof that specifically recognizes an FPB peptide defined by an amino acid sequence indicated in SEQ ID NO:1, SEQ ID NO:2, SEQ ID NO:3, SEQ ID NO:4, SEQ ID NO:5 or SEQ ID NO:6; detecting the presence or amount of FPB:detection agent complex present in the sample to determine whether the patient has thrombotic or thromboembolic disease.

Moreover, the present invention provides a diagnostic method for monitoring the treatment of thrombotic or thromboembolic disease in a patient by monitoring changes in the levels of FPB in the patients urine. Such monitoring may involve contacting urine samples suspected of containing fibrinopeptide B (FPB) and des-arginine FPB with an amount of detection agent specific for FPB to form an FPB:detection agent complex; wherein the detection agent is an antibody or fragment thereof that specifically recognizes an FPB peptide defined by an amino acid sequence indicated in SEQ ID NO:1, SEQ ID NO:2, SEQ ID NO:3, SEQ ID NO:4, SEQ ID NO:5 or SEQ ID NO:6; and monitoring the changes in the urine concentration of FPB over time to determine if the thrombosis or embolism is diminishing in size.

The present invention also provides for kits that contain in one or more containers one or more of the reagents or compositions used in carrying out the assays of the invention. These kits may also contain calibration samples or standards.

BRIEF DESCRIPTION OF DRAWINGS

FIG. 1A: Various concentrations of native human FPB (diamonds) or canine FPB (squares) were pre-incubated separately with FPB antiserum and then applied to FPB-coated wells. After incubation, antibody binding to the wells was assessed as described in Methods. FPB used in the pre-incubation mixtures was derived from purified human or canine fibrinogen (2.5 mg/mL) that was clotted with thrombin (2 units/mL) for one hour at room temperature. The clot liquor was then subjected to centrifugal ultrafiltration, and the presence of FPB in the ultrafiltrate was confirmed by HPLC. FPB concentrations are given in arbitrary units (AU). Data are presented as the mean±range of duplicate determinations. FIG. 1B: Various concentrations of purified human fibrinogen (closed circles), synthetic FPB (diamonds), des-arg FPB (triangles), or FPA (open circles) were pre-incubated separately with FPB antiserum and then applied to FPB-coated wells. After incubation, antibody binding to the wells was assessed as described in Methods. Data are presented as the mean of duplicate determinations and expressed as a percentage of the maximal absorbance obtained when no competitor was present in the pre-incubation mixture.

DETAILED DESCRIPTION OF THE INVENTION

Figure 1A:
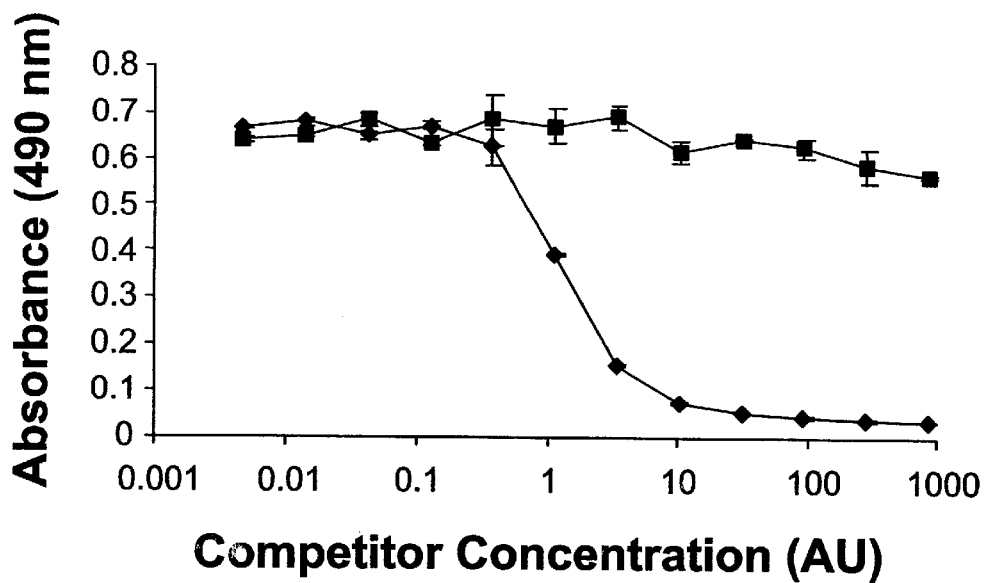
FIGS. 1A–1B. Specificity of FPB Antiserum by Competitive ELISA.

Fibrinopeptides are released at rapid rates during formation of fibrin clots and blood/urine fibrinopeptide levels are, therefore, accurate measures of thrombus propagation in thrombembolic disease. Fibrinopeptides A and B (FPA and FPB) are short amino acid sequences situated at the amino termini of the alpha and beta chains (respectively) of soluble fibrinogen. In one of the final steps in the coagulation pathway, thrombin converts soluble fibrinogen to fibrin by first cleaving off FPA to form fibrin I, which spontaneously polymerizes. Thrombin then releases fibrinopeptide B (FPB) from the beta-chains of the fibrin I subunits to form fibrin II polymers, which laterally associate and cross-link to form a semi-solid network, while the fibrinopeptides remain soluble in plasma.

Plasma FPA levels are elevated during thrombosis and this measurement could represent a valid marker for thrombosis and anticoagulation. FPA is, in fact, detectable in plasma by immunoassays and by high-performance liquid chromatography (HPLC). However, FPA is so easily cleaved from fibrinogen that artifactually elevated plasma levels are a common confounding problem. Even when collection tubes are supplemented with proteolytic inhibitors, the sampling procedure itself can cause FPA release. Falsely elevated levels have been associated with factors such as venipuncture techniques and phlebotomy through indwelling catheters.

The inventors have discovered that FPB is better suited as a marker of thrombotic activity than FPA. Without being bound by theory, it is believed that some of the advantages of FPB as a marker are associated with some of the properties of FPB that are described below. The kinetics of thrombin-mediated cleavage of FPB from fibrinogen are much slower than for FPA (Ng et al. 1993). In fact, there is evidence that thrombin-mediated FPB release occurs only after FPA removal from fibrinogen is complete. Further, the release of FPB ex vivo may be prevented by agents which inhibit fibrin I polymerization. Plasma measurement of FPB is therefore less prone to artifactual error. FPB is continuously cleaved from fibrinogen molecules during fibrin polymerization in vivo. Once polymerization is halted by the administration of systemic anticoagulation therapy, FPB cleavage ceases. Previous studies have shown that plasma FPB levels rise sharply following intrauterine thrombosis, thereby reflecting ongoing fibrin formation in vivo. Furthermore, FPB levels are not significantly elevated in a variety of other diagnoses. Thus, the fibrin formation associated with active thrombosis leads to significantly higher plasma levels of FPB than are seen in other medical conditions. Thus, FPB is less susceptible than FPA to artifactual elevation during sample collection. Measurement of plasma FPB levels is therefore a more sensitive and specific serologic marker for acute thrombosis.

The present efforts to measure active in vivo thrombosis focused on demonstrating that removal of FPB from fibrinogen on the surface of thrombi in situ correlated with local thrombotic activity and was extinguished during anticoagulation. First, in vitro experiments were performed showing that $beta_{15-22}$, the neo-epitope exposed on the beta-chain of fibrin after cleavage of FPB, is only transiently accessible to binding by a monoclonal antibody (anti-$beta_{15-22}$) (Morris et al. 1997a). This phenomenon was explained by the fact that the $beta_{15-22}$ site is rapidly covered up by lateral associations between parallel fibrin monofilaments. Thus, fibrin subunits are only able to bind anti-$beta_{15-22}$ when FPB has been cleaved off, but lateralization has not yet occurred. Essentially, the epitope is only accessible during active thrombosis.

Next, it was demonstrated that cleavage of FPB from fibrinogen also correlated with in vivo thrombotic activity. In an in vivo experimental model of DVT and PE, actively propagating in situ thrombi bound radio-labeled anti-$beta_{15-22}$ in sufficient quantities to be imaged with a gamma camera (Morris et al. 1993). Because the $beta_{15-22}$ site is only transiently exposed (prior to lateralization of the fibrin network), imaging of thrombi occurs only when coagulation is ongoing. Systemic anticoagulation of subjects with pre-formed thrombi, prior to radiolabeled anti-$betas_{15-22}$ administration, suppressed antibody binding. In fact, the degree of anticoagulation (as measured by blood heparin levels) had a strong inverse correlation with localization of radiolabeled anti-$beta_{15-22}$ at the thrombi (Morris et al. 1997b).

A similar model of thrombosis was used to compare the anti-thrombotic efficacies of four different anticoagulant regimens: intravenous unfractionated heparin, subcutaneous unfractioned heparin and two low molecular weight heparin, both given subcutaneously (Morris et al. 1998). There were significant differences in anti-thrombotic effect among regimens, which did not correlate with ex vivo anticoagulant tests (such as anti-Xa activities) measured during the experiments.

The measurement of the exposure of the $beta_{15-22}$ site as an indicator of thrombosis is problematic due to the transient nature of the exposure and by the fact that the measurement requires the infusion of detecting agents systematically. By contrast, we have now found that measurement of the released FPB peptide is an excellent indicator of thrombotic activity and does not have the disadvantages described for $beta_{15-22}$. Measurements of FPB in both in vitro and in vivo models of thrombosis were taken using high performance liquid chromatography (HPLC). Synthetic human FPB was easily distinguished from synthetic FPA and other plasma proteins. Next, plasma samples from three dogs, in which experimental thrombi had been induced, were pooled and analyzed by HPLC. Fibrinopeptide concentrations were estimated by comparing the areas under the peaks ($A_{205}$ time) to those obtained by treating known amounts of purified canine fibrinogen with thrombin. Peaks corresponding to both FPA and FPB were low prior to thrombus induction, but steadily increased as thrombi were induced and allowed to propagate in situ. These experiments support the validity of using FPB levels as a measure of in vivo thrombosis.

The invention involves, in part, the creation of a non-invasive blood, plasma, and/or urine test to detect active thrombosis, based on the measurement of FPB and/or des-arginine FPB (a degradation product that is formed rapidly as FPB is exposed to carboxypeptidases in normal plasma). Methods that can be used to carry out this measurement include peptide sequencing, mass spectrometry, chromatography (e.g., HPLC or TLC), electrophoretic separation (e.g., capillary electrophoresis) and measurement through specific binding interactions (e.g., immunoassays). Both FPB and des-arginine FPB may be measured. The invention also includes an immunoassay for measuring FPB and des-arginine FPB in these matrices.

The rationale for testing both peptides with the same assay is that, in humans, carboxypeptidases present in vivo in normal plasma degrade circulating FPB into des-arginine FPB. The relative proportions of FPB and des-arg FPB present in the plasma depend, in part, on each individual's carboxypeptidase activity. Elevated levels of both peptides in the plasma reflect the rate of ongoing thrombosis. Therefore, in one embodiment of the invention, the measurement of FPB is carried out using an immunoassay that is designed to cross-react with both FPB and des-arginine FPB. Alternatively, the two peptides may be measured through the use of two independent assays each specific for one of the peptides; the total amount of FPB derived peptides is then determined by summing the calculated concentrations of FPB and des-arginine FPB.

Thus, the present invention provides methods for measuring FPB in the blood and in the urine as markers of ongoing thrombosis for use in the diagnosis of DVT, PE and other thrombotic disorders. In addition, the assays can be used to determine the anti-thrombotic efficacy of different anticoagulation regimens. The FPB test is more sensitive and specific for the presence of active DVT or PE than the D-dimer test. It can be performed using urine, so venipuncture is not necessary.

An important aspect of the invention is the present discovery of the utility of measurements of FPB in urine.

Despite the fact that FPB is generated in blood, it has been found that the levels of FPB in urine are approximately one to two orders of magnitude greater than in blood or plasma and are thus amenable to measurement with simpler, faster, and/or less sensitive assays. Furthermore, in some cases the measurement of FPB in urine has, suprisingly, been found to correlate better with thrombotic activity or disease (relative to measurements in blood or plasma). An additional benefit of urine measurements is the fact that the time constant for changes in FPB concentration associated with thrombotic activity tends to be longer in urine than in blood; urine measurements are therefore not only indicative of current thrombotic activity but will also indicate thrombotic activity in the recent past.

An immunoassay test for the total concentration of FPB and des-arg FPB has been developed and the reagents have been or can be produced in mass quantities easily. The assay has been tested in in vitro models of thrombosis; in animal models using experimentally induced deep venous thrombi (DVT) and pulmonary emboli (PE) and in a human clinical study, where it has reliably detected the presence of DVT and PE in hospitalized patients. The invention can be used as a point-of-care diagnostic tool to detect and assist in the management of DVT and PE. The immunoassay can be performed easily and inexpensively at the patient's bedside. In addition, since the assay detects ongoing thrombus propagation, it is also useful for guiding therapy.

For purposes of more clearly and accurately describing the invention herein, certain terminological conventions have been adopted in the following discussion. These conventions are intended to provide a practical means for enhancing description of the invention, but are not intended to be limiting, and the skilled artisan will appreciate that other and additional, albeit not inconsistent, interpretations can be implied.

An "analog" or "variant" of FPB is a polypeptide that is not completely identical to native FPB. Such an analog of FPB can be obtained by altering the amino acid sequence by insertion, deletion or substitution of one or more amino acids. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spatial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains. L. Stryer, *Biochemistry* (2d ed.) p. 14–15; Lehninger, *Biochemistry*, p. 73–75.

It is known that analogs of polypeptides can be obtained based on substituting certain amino acids for other amino acids in the polypeptide structure in order to modify or improve biologic activity, such as antigenic or immunogenic activity. For example, through substitution of alternative amino acids, small conformational changes may be conferred upon a polypeptide which result in increased activity. Alternatively, amino acid substitutions in certain polypeptides may be used to provide residues which may then be linked to other molecules to provide peptide-molecule conjugates which retain sufficient biologic properties of FPB. Certain analogs that are linked to labels or solid phases but retain the ability to bind to anti-FPB antibodies, may be used as competitors in competitive immunoassays for FPB.

The degree of homology (percent identity) between a native and a variant sequence may be determined, for example, by comparing the two sequences using computer programs commonly employed for this purpose. One suitable program is the GAP computer program described by Devereux et al. (*Nucl. Acids Res.* 12:387, 1984), which is available from the University of Wisconsin Genetics Computer Group.

The amino acid sequence of the analog of FPB corresponds essentially to the native FPB amino acid sequence. As used herein "corresponds essentially to" refers to a polypeptide sequence that will elicit a biological response substantially the same as the response generated by native FPB. Such a response may be at least 60% of the level generated by native FPB, and may even be at least 80% of the level generated by native FPB. A variant of the invention may include amino acid residues not present in the corresponding native FPB or deletions relative to the corresponding native FPB.

An amino acid is "operably linked" when it is placed into a functional relationship with another amino acid sequence. Generally, "operably linked" means that the amino acid sequences being linked are contiguous An "antibody" in accordance with the present specification is defined broadly as a protein that binds specifically to an epitope. Monoclonal antibodies may be produced by methods known in the art. These methods include the immunological method described by Kohler and Milstein (1975) and by Campbell (1985); as well as the recombinant DNA method described by Huse et al. (1989).

As used herein, the term "monoclonal antibody" (or "mAb") refers to any homogeneous antibody or antigen-binding region thereof that is reactive with, preferably specifically reactive with, a single epitope or antigenic determinant. The term "monoclonal antibody" as used herein may, however, refer to homogeneous antibodies that are native, modified, or synthetic, and can include hybrid or chimeric antibodies. The term does not include "polyclonal antibodies," as that term is commonly understood. A "polyclonal antibody" is a group of heterogeneous antibodies that all recognize a single epitope or antigenic determinant.

The term "antigen-binding region" refers to a naturally occurring, modified, or synthetic fragment of an antibody of the invention that is reactive with an epitope. Such antigen-binding regions include, but are not limited to, Fab, $F(ab')_2$, and Fv fragments.

Functional equivalents of the antibody of the invention further include fragments of antibodies that have the same binding characteristics as, or that have binding characteristics comparable to, those of the whole antibody. Such fragments may contain one or both Fab fragments or the $F(ab')_2$ fragment. Preferably, the antibody fragments contain all six complement determining regions ("CDRs") of the whole antibody, although fragments containing fewer than all of such regions, such as three, four or five CDRs, may also be functional. Fragments may be prepared by methods described by Lamoyi et al. (1983) and by Parham (1983). Other functional equivalents of the antibody of the invention include other molecules that specifically bind FPB, for example, receptors that bind FPB and peptides or nucleic acids that have been selected for their ability to bind FPB (e.g., by phage display or SELEX methods).

The antibodies of the present invention have been found to be specifically reactive with an epitope FPB, which is found in a plurality of related protein moieties, including intact fibrinogen as well as fragments thereof, including fibrinopeptide B, des-Arg fibrinopeptide B, the N-DSK fragment of fibrinogen resulting from cleavage with cyanogen bromide, and the peptides defined by SEQ. ID. NOs:1 and 2. The term "anti-FPB" refers to the ability of the antibody of the present invention to react specifically with this epitope, which is characteristic of fibrinogen, fibrinopeptide B, des-Arg fibrinopeptide B, N-DSK, and related peptides.

Accordingly, the antibodies of the invention is specifically reactive with an epitope defined by an amino acid sequence characteristic of SEQ ID NOs:1 and 2, and other functionally equivalent sequences, i.e., those amino acid sequences that exhibit similar binding capacities. The antibody is not significantly cross-reactive with moieties lacking the defining epitope.

Among other properties of the antibody of the invention, it is demonstrated herein that the antibody is reactive with peptides defined by SEQ ID NOs:1 and 2, which differ at their N-termini from native FPB, as well as with SEQ ID NOs 3–6, which are native forms of FPB found in physiological samples. Accordingly, the antibody of the invention is understood to react specifically with an epitope defined by the amino acid sequence CQGVNDNEEGFFSAR (SEQ ID NO:1) and CQGVNDNEEGFFSA (SEQ ID NO:2). Proteins containing SEQ ID NO:1 or SEQ ID NO:2, or similar sequences, (for example: QGVNDNEEGFFSAR (SEQ ID NO:3); QGVNDNEEGFFSA (SEQ ID NO:4); cyclised pyroglutamic acid-GVNDNEEGFFSAR (SEQ ID NO:5); and cyclised pyroglutamic acid-GVNDNEEGFFSA (SEQ ID NO:6)) within their primary structures, and lacking significant steric interference from higher order structures will, therefore, bind with one or more of the detecting antibodies or polyclonal antisera of the invention. Such proteins may be naturally occurring, such as Fibrin I, or synthetically made, e.g., produced by conventional synthetic or recombinant methods such as are known in the art. Homologs of the amino acid sequence characterized by SEQ ID NOs:1 and 2, and proteins containing the epitope-defining sequence, are also expected to be reactive with one or more of the detecting antibodies or polyclonal antisera of the invention. However, the antibodies and antisera exhibit no substantial cross-reaction with moieties lacking this epitope. Peptides or proteins containing this epitope can be detected using the immunoassay of the invention, can be used as calibrators or standards, or can be labeled or immobilized and used as competitors in immunoassays for FPB.

The term "fibrinogen" without more is intended to include any type of fibrinogen. Fibrinogen, therefore, refers to monomeric and dimeric fibrinogen molecules having the monomer structure (AαBβγ), as well as molecules having the monomer structure (Aα $_E$Bβγ), and other hybrid molecules, whether naturally occurring, modified, or synthetic. The term "fibrinogen" refers generally to fibrinogen from humans, but may include fibrinogen of any species, especially mammalian species. In addition, the term may be specifically limited to a particular species in particular contexts, such as "human fibrinogen."

Generally, to be useful as an immunogen, a peptide fragment must contain sufficient amino acid residues to define the epitope of the molecule being detected. If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a thiol-reactive moiety on the carrier molecule such as a cysteine residue or a maleimide group. In the present invention, a cysteine residue has specifically been covalent attached to the amino-terminus of the molecule so as to provide the necessary cysteine. Further, by attaching the cysteine to the amino-terminus, the carrier molecule will preferentially attach to this particular end, allowing the antigenic carboxy-end to be exposed.

The present invention provides animals that produce polyclonal antibodies reactive with an epitope of fibrinopeptide B and fibrinogen and fragments thereof containing the epitope. The invention also provides hybridoma cell lines that produce monoclonal antibodies reactive with an epitope of fibrinopeptide B and fibrinogen and fragments thereof containing the epitope. The antibodies produced by these animals and hybridomas are also important aspects of the invention.

The hybridoma technology originally described by Kohler and Milstein (1975) can be used to prepare hybridoma cell lines whose secretory product, monoclonal antibodies, are reactive with an epitope or antigenic determinant of fibrinopeptide B. A general method of preparing hybridoma cell lines of the invention is described below. Those skilled in the art will recognize that the present invention, including the monoclonal antibodies and hybridoma cell lines described in detail herein, provide a variety of ways to make the hybridomas, and thus the antibodies of the invention. Hybridoma cell lines of the invention can be prepared using the fibrinopeptide B peptide defined by SEQ ID NO:1 or a desarginine-FPB peptide defined by by SEQ ID NO:2 for activation of immunologically relevant spleen cells. Generally, a host mammal is inoculated with a peptide or peptide fragment as described above, and then boosted. Spleens are collected from inoculated mammals a few days after the final boost. Antibody-producing spleen cells are then harvested and immortalized by fusion with mouse myeloma cells. The hybrid cells, called hybridomas, are continuous cell lines resulting from the fusion, which are then selected and screened for reactivity with the peptide. The artisan is referred to Kohler and Milstein (1975); Kennett et al. (1980); and Goding (1986) for further details on hybridoma technology. See also Campbell (1985).

The specific anti-FPB antibodies described herein are merely illustrative of the invention, and all antibodies that are specifically reactive with the fibrinopeptide B peptide defined by SEQ ID NO:1 or the desarginine-FPB peptide defined by by SEQ ID NO:2, regardless of species of origin or immunoglobulin class or subclass designation, including IgG, IgA, IgM, IgE, and IgD, are included in the scope of this invention. The present invention also provides antigen-binding fragments of the anti-FPB antibodies. The ability to bind to fibrinopeptide B as opposed to non-FPB-containing substances is a general characteristic of the specific antibodies according to the present invention.

As discussed above, antibodies of the invention can be constructed and isolated by immunization of animals, preparation of hybridomas, and identification of antibodies with a reactivity to fibrinopeptide B and fibrinogen similar to that of the anti-FPB antibodies described. However, the present invention also provides means for identifying monospecific antibodies of the invention that does not require determination of antibody reactivity with a broad number of Bβ-related fragments. Antibodies of the invention can be identified also by immunoprecipitation and competitive binding studies using the antibody produced by the cell lines described herein.

Immunoprecipitations using the anti-FPB monospecific antibody can be used to determine antigenic identity. Confirmation of identity can be obtained by depleting the antigen from testable samples such as plasma samples, using excess amounts of one anti-FPB antibody and observing the inability of another antibody to immunoprecipitate a Bβ-chain fragment from the treated sample. Also, in instances in which the antibodies bind with the same epitope or closely associated epitopes, each antibody will compete with the other(s) for binding to fibrinopeptide B. Competitive binding studies are generally known in the art, and one conventional type is presented in the examples below.

Treatment of antibody preparations with proteolytic enzymes such as papain and pepsin generates antibody fragments, including the Fab and F(ab')$_2$ species, that retain antigen-binding activity. Treatment of the antibodies of the invention with such enzymes can therefore be used to generate fibrinopeptide B antigen-binding fragments of the invention. The preparation of antigen-binding fragments of the antibodies of the invention and their diagnostic and therapeutic usefulness, as well as other applications, suggest themselves to the skilled artisan. Antigen-binding fragments of the anti-FPB antibody are especially useful in therapeutic embodiments of the present invention.

Those skilled in the art will recognize that the antigen-binding region of the antibodies and antibody fragments of the invention is a key feature of the present invention. The anti-FPB hybridoma cells of the invention serve as a preferred source of DNA that encodes such antigen-binding regions of the invention. This DNA, through recombinant DNA technology, can be attached to DNA that encodes any desired amino acid residue sequence to yield a novel "hybrid," or "chimeric," DNA sequence that encodes a hybrid, or chimeric, protein. In such a fashion, chimeric antibodies of the invention, in which one portion of the antibody is ultimately derived from one species and another portion of the antibody is derived from another species, can be obtained. However, the present invention also comprises any chimeric molecule that contains an FPB antigen-binding region.

Antibodies of the present invention can also be labeled by conjugation to any detectable group, such as fluorescent labels, enzyme labels, and radionuclides to identify expression of fibrinogen, or cleavage products including fibrinopeptide B or parts thereof. Suitable detectable labels may be selected from among those known in the art, including, but not limited to, radionuclides, enzymes, specific binding pair components, colloidal dye substances, fluorochromes, reducing substances, latexes, digoxigenin, metals, particulates, dansyl lysine, antibodies, protein A, protein G, electron dense materials, chromophores, electrochemiluminescent substances, chemiluminescent substances, electroactive substances and the like. Effectively, any suitable label, whether directly or indirectly detectable, may be employed. One skilled in the art will clearly recognize that these labels set forth above are merely illustrative of the different labels that could be utilized in this invention.

Methods for labeling antibodies have been described, for example, by Hunter et al. (1962) and by David et al. (1974). Additional methods for labeling antibodies have been described in U.S. Pat. Nos. 3,940,475 and 3,645,090.

The label may be radioactive, i.e., contain a radionuclide. Some examples of useful radionuclides include $^{32}P$, $^{125}I$, $^{131}I$, $^{111}In$, and $^3H$. Use of radionuclides have been described in U.K. patent document No. 2,034,323, U.S. Pat. Nos. 4,358,535, and 4,302,204.

Some examples of non-radioactive labels include enzymes, chromophores, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, and by Rotman (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol and luminescent bipyridyl or phenanthrolyl containing complexes of ruthenium or osmium.

The labels may be conjugated to the antibody probe by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate. Alternatively, labels such as enzymes and chromophoric molecules may be conjugated to the antibodies by means of coupling agents, such as dialdehydes, carbodiimides, dimaleimides, and the like.

The label may also be conjugated to the antibody probe by means of a ligand attached to the probe by a method described above and a receptor for that ligand attached to the label. Any of the known ligand-receptor combinations is suitable. Some suitable ligand-receptor pairs include, for example, biotin-avidin or -streptavidin, and antibody-antigen. The biotin-avidin combination is preferred. Thus, the anti-FPB antibodies of the invention can be derivatized by conjugation to biotin, and used, upon addition of species of avidins that have been rendered detectable by conjugation to fluorescent labels, enzyme labels, radionuclides, electron dense labels, substrates, etc., in a multiplicity of immunochemical and immunohistological applications.

The antibodies of the invention may also be attached or bound to substrate materials according to methods known to those skilled in the art. Such materials are generally substantially solid and relatively insoluble, imparting stability to physical and chemical disruption of the antibodies, and permitting the antibodies to be arranged in specific spatial distributions. Among substrate materials, materials may be chosen according to the artisan's desired ends, and include materials such as gels, hydrogels, resins, beads, magnetic particles or beads, nitrocellulose, nylon filters, microtiter plates, culture flasks, polymeric materials, and the like, without limitation.

The antibodies of the present invention, whether labeled or unlabeled, can be used in immunological assays to determine the presence of fibrinogen or FPB-associated peptides in tissue samples from human or animal subjects. Fluid samples of subjects, such as plasma or urine, as well as samples from blood banks, can be evaluated for the presence of fibrinogen and FPB using an anti-FPB antibody of this invention. Moreover, suitable pharmaceutical preparations according to the invention may be employed for in vivo use, such as for the visualization of fibrinogen or FPB-containing substances and structures in a living subject.

Thus, the invention provides a method for binding fibrinopeptide B, fibrinogen or a fragment thereof comprising the amino acid sequence defined by SEQ ID NOs:1 and 2 by means of the anti-FPB monospecific antibody. Accordingly, fibrinogen and fibrinopeptide B, natural, modified, and synthetic variants thereof, as well as fragments thereof, may be detected and measured by means of the antibodies of the invention.

In the FPB binding method of the invention, the method includes contacting a testable system, in which the presence or absence of FPB is to be determined, with a composition comprising an anti-FPB antibody or antigen-binding region thereof. The method then involves measuring an amount of specific association or binding between an analyte of the testable system and the antibody. In this method, specific binding of the antibody in the system indicates the presence of the analyte, i.e., fibrinogen or FPB-containing fragments thereof in the system The present invention further provides a method of detecting the presence of fibrinopeptide B in a sample. The method involves use of a labeled probe that recognizes protein/peptide present in a biological sample such as a blood or urine sample. The probe may be an antibody according to the invention that recognizes FPB-containing analytes present in the sample. Other testing methods known in the art can be adapted to use the antibody of the invention.

A typical method involves the differential separation of degradation products, such as separation of the products by ultracentrifugation. The products are then measured by contacting the products with antibodies that are specifically reactive with or specifically associate with one or more domains of fibrinogen. Preferably, such antibodies are specifically reactive with a single degradation product, thereby permitting characterization of the product in relation to other products.

In one embodiment, the detection method employs a anti-FPB antibody that has been detectably labeled with a marker moiety. In other embodiments, the method may employ an antibody of the invention that has been bound to a substrate material. In the method, the composition may also include other reagents such as other antibodies that differentially detect other fibrinogen subunits or subtypes. This method can be further adapted for use with at least one other antibody having specificity for alternative fragments, permitting differential analysis or characterization of free FPB or of FPB-containing fragments and other fragments in the same sample. For example, two or more antibodies conjugated to distinct fluorescent labels can be employed as probes in protein separations or other immunometric techniques.

The FPB binding method of the invention includes methods known in the art that employ antibodies to bind target substances specifically. Preferred methods include immunochemical methods, such as enzyme-linked immunosorbent assay (ELISA) methods, western blot, immunonephelometry methods, agglutination methods, precipitation methods, immunodiffusion methods, immunoelectrophoresis methods, immunofluorescence methods, radioimmunoassay methods, surface plamon resonance, and immunoassay methods based on the detection of chemiluminescent, fluorescent, phosphorescent, electrochemiluminescent, bioluminescent or electroactive compounds.

Assays for detecting the presence of proteins with antibodies have been previously described, and follow known formats, such as standard blot and ELISA formats. These formats are normally based on incubating an antibody with a sample suspected of containing the protein and detecting the presence of a complex between the antibody and the protein. The antibody is labeled either before, during, or after the incubation step. The protein is preferably immobilized prior to detection. Immobilization may be accomplished by directly binding the protein to a solid surface, such as a microtiter well or bead, or by binding the protein to immobilized antibodies.

Methods for conducting immunoassays are well known. Techniques that can be used include direct binding formats and competitive binding formats. One common example of the direct binding format is the sandwich binding assay. In a typical example of a competitive assay for FPB, FPB in a sample competes with labeled FPB (or an analog thereof) for binding to a labeled anti-FPB antibody. In some common "solid phase" binding assay formats, the label one of the two labeled species is a solid phase support or a capture moiety that is used to bring the reagent onto a solid phase support. Examples of appropriate immunoassay techniques may be found in the Immunassay Handbook, Wild D., Editor, Stockton Press: New York, 1994, hereby incorporated by reference.

The invention further includes a method for determining or diagnosing the existence of thrombotic or thromboembolic disease, such as deep thrombosis or pulmonary embolism in a subject. In this method, FPB or a fragment thereof is measured by means of a composition including an anti-FPB antibody of the invention. The measured amount of the FPB analyte is compared with an amount of FPB that is recognized or known to be associated with thrombotic or thromboembolic disease. The method then involves the determination from the measured and standard value(s) of FPB the presence or likelihood of thrombotic or thromboembolic disease in the subject. The method can include measuring or detecting FPB peptides in vivo, such as by imaging or visualizing the location and/or distribution of fibrinopeptide B, in the body. Alternatively, the method includes obtaining a medical sample from the subject and measuring FPB ex vivo or in vitro.

Polyclonal Antisera
Peptide Synthesis

An analogue of human fibrinopeptide B (FPB) containing a cysteine residue at the amino terminal end of the peptide was prepared by Peninsula Laboratories (San Carlos, Calif.). The peptide was designed to permit directional coupling to maleimide-activated carrier protein for immunization of rabbits. Peptide purity was >90% as judged by mass spectral analysis and by HPLC using two different solvent systems. The amino acid sequence of the peptide is as follows: CQGVNDNEEGFFSAR (SEQ ID NO:1). An analogue of des-arginine FPB (amino acid sequence: CQGVNDNEEGFFSA, (SEQ ID NO:2)) was prepared in a similar fashion.

Preparation of FPB Antisera

An immunoconjugate of human FPB was prepared by coupling 5 mg of N-cysteinyl-FPB to 10 mg of maleimide-activated keyhole limpet hemocyanin (Pierce Chemical, Rockford, Ill.) according to a protocol provided by Pierce (Protocol #0135). Polyclonal antiserum to FPB was raised in New Zealand White rabbits. Three rabbits each received a primary subcutaneous injection of immunoconjugate (one mg) in complete Freund's adjuvant followed by two subcutaneous booster injections (one mg each) in incomplete Freund's adjuvant given at four week intervals. Rabbits were bled at two-week intervals starting two weeks after the primary injection. After allowing the blood to clot overnight at 4 C., antiserum was collected by centrifugation (2000×g, 10 min) and stored at −20 C. until analyzed. The FPB antibody titer of each antiserum was determined in a direct-binding ELISA. Briefly, microplate wells were coated with synthetic human FPB (Sigma Chemical, St. Louis, Mo.) and blocked with BSA. Wells were then incubated with serial dilutions of FPB antiserum followed by peroxidase-conjugated goat anti-rabbit IgG detecting antibody (Jackson ImmunoResearch Laboratories, West Grove, Pa.). Wells were developed with o-phenylenediamine (OPD) substrate solution, and the absorbance (490 nm) of each well was measured in a microplate reader (Molecular Devices, Sunnyvale, Calif.). The antibody titer was arbitrarily defined as the minimal antiserum dilution resulting in an absorbance of >1.0. The process was repeated on separate rabbits using an immunoconjugate of des-arginine FPB and keyhole limpet hemocyanin.

Specificity of the Antiserum

A competitive ELISA was developed to evaluate the specificity of the FPB antiserum. Unless otherwise noted, all steps were performed at room temperature, and the microplates were washed three times in between each step with 0.02 M $NaH_2PO_4$, 0.15 M NaCl, 1 mM EDTA, pH 7.4 (PNE) containing 0.1% tween-20. Microplate wells were first coated with synthetic human FPB (2 mg/mL in 0.2 M $NaHCO_3$, 100 mL/well) overnight at 4 C., and then "blocked" with 1% BSA in PNE (PNEA) for one hour. Meanwhile, serial dilutions of each competitor were prepared. The following competitors, all of human origin except where noted, were tested: native FPB (human and canine), synthetic FPB, synthetic des-arg FPB, synthetic fibrinopeptide A, and purified fibrinogen. Twenty mL of each competitor dilution were pre-incubated separately with 200 mL of FPB antiserum (1:2500) in polypropylene microfuge tubes for 90 min. Dilutions of the competitors and of antiserum were prepared in dilution buffer (PNEA containing 0.1% tween-20). At the end of the pre-incubation period, 100 mL of each mixture were applied to duplicate FPB-coated wells and incubated for 90 min. After washing, 100 mL of peroxidase-conjugated goat anti-rabbit IgG detecting antibody (1:5000 in dilution buffer) were added to each well and incubated for one hour. After a final wash, each well was developed with 100 ml of OPD substrate solution for exactly five minutes. The reaction was stopped by addition of an equal volume of 3 N $H_2SO_4$, and the absorbance (490 nm) of each well was measured in the microplate reader.

Although high titers were demonstrated for several antisera, and the present invention includes any antisera produced in this fashion, the best reactivity profile obtained by the inventors to-date is was disclosed for R4097, bleed I3. Competition experiments using this antiserum indicated that native human FPB in solution was an effective competitive inhibitor of antibody binding to surface-bound synthetic human FPB. In contrast, native canine FPB in solution did not compete for antibody binding to surface-bound synthetic human FPB suggesting that canine FPB does not cross-react with the antiserum. The cross-reactivity of des-arg FPB, defined as IC50 of FPB (6.7 nM) divided by IC50 of des-arg FPB (8.9 nM) times 100, was 75%. Thus, the FPB assay is sensitive to both FPB and its primary metabolite, des-arg FPB. FPA exhibited essentially no cross-reactivity (<0.1%).

The antiserum showed significant cross-reactivity to parent (human) fibrinogen. The IC50 of fibrinogen (2.3 nM) was about one-half the IC50 of FPB, not unexpected since each fibrinogen molecule harbors two potentially cross-reacting FPB sequences. It is, therefore, preferable to remove cross-reacting fibrinogen molecules (340,000 kD) from plasma and urine samples by centrifugal ultrafiltration. Fibrinogen can be separated from fibrinopeptides in solution using a variety of filtration membranes, with molecular weight cutoffs ranging from 50,000–100,000 kD. However, the best results were obtained using centrifugal ultrafiltration with Biomax-100 membranes (100,000 kD cut-off). It is important to note that other polyclonal antisera produced using this method in additional animals did not cross-react with fibrinogen. The invention also includes the use of this antisera in immunoassays, in which case fibrinogen would not need to be removed from the patient samples.

Monoclonal Antibodies

Conjugation of Peptide: N-cysteinyl FPB (or des-arg FPB) is conjugated to maleimide-activated keyhole limpet hemocyanin as previously described. Five Balb/c mice are each immunized with a 50 ug priming dose followed by several boosting doses of 50 ug each. Test bleeds are screened for antibody production and titer using the direct binding ELISA previously described.

A splenocyte fusion is performed on the best responder as determined by the direct binding and competitive ELISA. The lymphocytes are fused to an Sp2/0-Ag14 hybridoma cell line using an optimized polyethylene glycol-mediated fusion protocol. Expansion and Screening: Fused cells are plated into 96-well plates and monitored weekly for cell growth. Wells exhibiting cell growth are screened by ELISA at four weeks and then again at six weeks.

Cells from positive wells are harvested and subcloned by limiting dilution. Subclones are screened by ELISA. Positive subclones are expanded and screened again. The most promising clones, as determined by direct binding and competitive ELISA, are stored frozen and used for ascites production.

Ascites fluid is produced in Balb/c mice following intraperitoneal injection of the selected hybridoma cell line derived from subcloning. The fluid is screened (by ELISA) and subjected to antibody isotyping.

FPB/des-arg FPB Assays

The following procedure was found to be the most optimal one for determination of the fibrinopeptide B (FPB) concentration in ultrafiltered plasma and urine samples. In general, because of the high levels of FPB in urine, it is customary to run urine ultrafiltrates in the "standard assay" (see below) and plasma ultrafiltrates in the "sensitive assay". Note that the plasma ultrafiltrate starts out at a 1:2 dilution.

Materials used: anti-FPB antiserum (rabbit 4097, bleed I3); synthetic FPB control solution; FPB stock solution; IgG-HRP stock solution; Coating buffer (0.2 M sodium bicarbonate); wash buffer (0.02 M NaH2PO4, 0.15 M NaCl, 1 mM EDTA, pH 7.4, containing 0.1% tween-20); dilution buffer (0.02 M NaH2PO4, 0.15 M NaCl, 1 mM EDTA, pH 7.4, containing 1% BSA and 0.1% tween-20); Hydrogen peroxide, 30% (H2O2, Sigma #H1009); o-phenylene diamine tablets, 10 mg (OPD, Sigma #P8287); OPD solution A (0.5 M citric acid); OPD solution B (0.11 M sodium phosphate (dibasic)); OPD stop solution (3 N sulfuric acid); PNE 10×stock solution (0.2 M sodium phosphate (monobasic), 1.5 M sodium chloride, 10 mM EDTA (disodium salt), pH 7.4); PNEA (PNE (1×) containing 1% (w/v) bovine serum albumin); Tween-20 (Sigma #P6585); Tween-20, 10% (Sigma #P8942).

Methods

Microwell plates are prepared as follows: Dilute FPB stock solution to 2 mg/mL with coating buffer. Add 100 ul FPB solution (2 mg/mL) to each microplate well. Seal wells with a plate sealer and place in the refrigerator overnight.

The "standard assay" is used to detect FBP/des-arginine FPB concentrations of 1.56–100 ng/mL. The samples are prepared as follows: Dilute FPB stock solution to 2 mg/mL with CB. Add 100 ul FPB solution (2 mg/mL) to each microplate well. Seal wells with a plate sealer and place in the refrigerator overnight. Thaw ultrafiltered samples in a room temperature bath. Dilute anti-FPB antiserum 1:2500 with DB. Dilute FPB stock solution to 100 ng/mL with DB and then make two-fold serial dilutions (501+501 DB) using the P200. Use the following FPB concentrations for the standard curve: 100, 50, 25, 12.5, 6.25, 3.13, 1.56, and 0 ng/mL. Dilute FPB control 1:2,000 with dilution buffer. Combine 20 ul standard/control/sample with 200 ul anti-FPB (1:2500) in separate 1.7-mL microfuge tubes, vortex to mix. (These are referred to as pre-incubation mixtures.) Incubate 1 hr 45 min.

The "sensitive assay" is used to detect FBP/des-arginine FPB concentrations of 0.313–20 ng/mL. The samples are prepared as follows: Dilute FPB stock solution to 2 mg/mL with CB. Add 100 ul FPB solution (2 mg/mL) to each microplate well. Seal wells with a plate sealer and place in the refrigerator overnight. Thaw ultrafiltered samples in a room temperature bath. Dilute anti-FPB antiserum 1:250 with DB. Dilute FPB stock solution to 20 ng/mL with dilution buffer and then make two-fold serial dilutions (250 ul+250 ul dilution buffer). Use the following FPB concentrations for the standard curve: 20, 10, 5, 2.5, 1.25, 0.625, 0.313, and 0 ng/mL. Dilute FPB control 1:10,000 with dilution buffer. Combine 20 ul anti-FPB (1:250) with 200 $\mu$l standard/control/sample in separate 1.7-mL microfuge tubes, vortex to mix. (These are referred to as pre-incubation mixtures.) Incubate 1 hr 45 min.

During the antibody pre-incubation period, remove the FPB-coated plate from the refrigerator and rinse each well twice with 250 ul washing buffer. Add 100 $\mu$l PNEA to each well to "block" residual protein binding sites on the wells. Cover the plate and allow 1 hr to "block". At the end of the antibody pre-incubation period, rinse each well twice with 250 $\mu$l washing buffer.

The assays are performed as follows: Add 100 $\mu$l of each pre-incubation mixture to duplicate wells. Cover the plate and incubate 1 hr 15 min and then rinse each well three times with 250 $\mu$l washing buffer. Add 100 $\mu$l IgG-HRP (1:4000 in dilution buffer) to each well. Cover the plate and incubate 1 hr 15 min. At the end of the IgG-HRP incubation rinse each well three times with 250 $\mu$l washing buffer.

Complete the substrate solution by first dissolving a 10-mg OPD tablet in the OPD A/OPD B mixture and then adding 10 $\mu$l H202. Invert several times to mix. Add 100 $\mu$l substrate solution to each well. Incubate exactly 5 min and then add 100 $\mu$l OPD stop solution to each well.

Read the absorbance of each well in the Vmax microplate reader using the following instrument setup: dual wavelength end-point mode (L1 =490 nm, L2=650 nm), automix on. Read the plate 14 min after initiating the OPD substrate reaction. Generate a standard curve from a four-parameter fit of the FPB standards. Use Softmax to interpolate the FPB concentrations of the samples and the FPB control from the standard curve.

The invention will be further described by reference to the following detailed examples.

EXAMPLE 1

Measurement of FPB and des-arginine FPB in Plasma Samples

The objective of this experiment was to determine if the immunoassay could detect synthetic FPB and synthetic des-arginine FPB in the presence of normal human plasma. The assay was also used to measure FPB levels in serum (clotted plasma), serially diluted in anticoagulated plasma, in order to simulate the concentrations expected when a small thrombus releases FPB into the circulating blood volume Methods Known concentrations of synthetic FPB or des-arg FPB (0 to 100 ng/ml) diluted in buffer or anticoagulated, ultrafiltrated plasma were pre-incubated with a fixed dilution of high-titer anti-FPB antiserum for 90 minutes at room temperature in polypropylene tubes. These pre-incubation mixtures were then added to FPB-coated microplate wells and incubated for an additional hour at room temperature. The plates were then further developed with anti-rabbit IgG-HRP and OPD as described above. After measuring the absorbance at 490 nm, a standard curve is generated. Parallelism was evaluated by comparing standards diluted in buffer to standards diluted in plasma.

Results

The assay did not detect FPB in normal human anticoagulated plasma. When plasma was "spiked" with purified FPB (final concentration 10 ng/ml), the assay measured 7.72±0.89 ng/ml. Similar results were obtained using purified des-arginine FPB (results not shown). In addition, serum (obtained by clotting plasma with thrombin) was diluted (1:800) with plasma pretreated with an excess of heparin. The FPB concentration was 8.03±0.51 ng/ml, which is within the range one would expect if 1% of the plasma fibrinogen had been converted to fibrin. Anti-FPB did not cross-react with canine fibrinopeptides, or with canine intact fibrinogen (results not shown).

Discussion

These experiments validate the accuracy of the immunoassay for measuring FPB and des-arginine FPB. Furthermore, the FPB levelsmeasured would be able to detect a thrombosis of 0.1% of the total in vivo blood volume, which in a 70 kg person, would constitute a 4 ml thrombus.

Conclusions

The plasma FPB immunoassay is capable of detecting active thrombosis in vivo. The assay is useful for diagnosing DVT and PE, as well as for comparing the ability of anticoagulants to suppress clot propagation in vivo.

EXAMPLE 2

FPB Levels In An Animal Model Of Thrombosis

Objectives

In a well-established model used in previous experiments, plasma and urine samples from dogs during experimental thrombosis were analyzed to measure FPB levels. Prior to the induction of thrombosis, the animals were depleted of canine fibrinogen and transfused with purified human fibrinogen. Elevated levels of human FPB in the plasma and urine reflect thrombotic activity.

Methods

Adult mongrel dogs were anesthetized and their native fibrinogen depleted. After the ancrod has been eliminated from the circulation, during a time when the native fibrinogen activity is minimal, experimental thrombi are induced as previously described (Morris et al. 1997b). The dogs are anesthetized with halothane, intubated and mechanically ventilated to maintain arterial blood gases within normal limits. The animals received a bolus of tranexamic acid at this time and every 6 hours thereafter to completely inhibit fibrinolysis (Marsh et al. 1994). After this, they were transfused with 6 grams of purified human fibrinogen in normal saline to achieve a fibrinogen level of at least 300 mg/dl. Under these conditions, fibrinogen levels were maintained at >200 mg/dl throughout the study period.

Double balloon catheters were advanced via hind-leg saphenous veins to the femoral veins on each side. The balloons were then inflated, creating a 5 ml sealed chamber within the veins. Through a port between the double balloons, 200 units of thrombin were infused into each venous lumen to induce thrombosis. After one hour, all the balloons were deflated and the induced thrombi are aged in situ for an additional three hours.

For each animal, one balloon catheter was left in the femoral vein to prevent embolization of the thrombus. The balloon catheter in the contralateral femoral vein was removed and the thrombus was embolized by passive leg motion.

After embolization, anticoagulation was achieved with a heparin bolus (300 units/kg) followed by continuous infusion (90 units/kg/hr), adjusted to keep the plasma heparin level greater than 1.0 units/ml. Anticoagulation at this dose was associated with complete suppression of thrombus propagation (Morris et al. 1997b). In separate experiments, lower doses of heparin were used (80 units/kg loading dose and 18 units/kg/hr infusion rates) and the dose was adjusted to maintain a "therapeutic heparin level" (0.2–0.4 units/ml).

Blood and urine samples were collected into titrated tubes (containing protease inhibitors) at baseline, after defibrinogenation, at regular intervals after thrombus induction, and after anticoagulation. Plasma was obtained by centrifugation (2500×g for 10 minutes) and then subjected to ultrafiltration (Millipore) to remove fibrinogen and other plasma proteins. All samples were stored at 70 C. until analyzed. $FPB_{tot}$ levels in urine and ultrafiltrated plasma are determined by immunoassay as described above.

The means and standard deviations of the $FPB_{tot}$ levels, as determined by immunoassay, associated with each time point are calculated. Baseline values are compared to values during thrombus induction, propagation and anticoagulation. A difference between means of at least two standard deviations is considered statistically significant.

Results

Preliminary experiments were performed on three dogs, all of whom received anticoagulation with excess doses of heparin after embolization of the experimentally induced thrombi (see figure below). The measurements in the first few hours of the experiment demonstrate that transfusion of large amounts of human fibrinogen do not significantly elevate plasma or urine $FPB_{tot}$ levels, prior to thrombus induction.

However, after thrombi are formed in the deep veins, the plasma $FPB_{tot}$ levels immediately rise. Plasma $FPB_{tot}$ remains elevated above baseline during clot propagation. Another peak in the plasma $FPB_{tot}$ levels occurs immediately after embolization. Once excess heparin is begun, thrombosis is halted. FPB is no longer produced and the $FPB_{tot}$ remaining in the plasma clears rapidly ($t_{1/2}$ of approximately 45 minutes).

The total amount of $FPB_{tot}$ in the urine (measured at 30-minute intervals) was also low after human fibrinogen transfusion, but steadily rose after thrombi were formed. Predictably, the amount of $FPB_{tot}$ recovered in the urine paralleled the rise in plasma levels, albeit several hours later. The actual concentration of $FPB_{tot}$ in the urine was, in general, two orders of magnitude higher than the levels measured in the plasma, presumably reflecting preferential clearance of the peptide by the kidney.

Interestingly, FPB levels in both the plasma and urine increased after the thrombi were embolized, despite the fact that no further thrombin was infused. As before, the plasma levels rose immediately, whereas the amounts cleared in the urine rose several hours after the event.

Discussion

These experiments indicate that plasma and urine levels of FPB are potential markers of ongoing thrombosis in VTE. Preliminary data suggest that one or both of these levels will increase significantly during active thrombosis, but revert towards normal during increasingly intense anticoagulation regimens. These findings demonstrate the validity of FPB as a marker of thrombosis.

EXAMPLE 3

Fibrinopeptide B in a Model of Acute Pulmonary Embolism

The objectives of this experiment were to determine if the thrombotic activity of pulmonary embolism can be measured using a novel assay for plasma levels of fibrinopeptide B and to test the hypothesis that embolization itself causes pre-existing thrombi to thrombose further, possibly leading to clot enlargement and downstream micro-embolization.

The cardiopulmonary effects of major pulmonary embolism are incompletely understood. In particular the role of active thrombosis in the detrimental effects on the pulmonary circulation is not known. In fact, it has yet to be determined whether emboli in the high-flow circulation of the pulmonary arteries increase their thrombotic activity relative to the activity occurring prior to embolisation. Using a recently developed plasma marker for active thrombosis, fibrinopeptide B (FPB) the following experiments were performed to determine if the thrombotic activity of venous thrombi increases following embolisation.

Most patients with pulmonary emboli survive their illness when treated with "standard doses" of anticoagulants. However, a sub-population of patients with massive PE have a high mortality even when treated with standard anticoagulation and thrombolytics. The pathophysiology of their deaths is not clear, since a large proportion of patients die several days after the initial event and the size of the embolization does not directly predict mortality. It is hypothesized that embolization itself promotes further thrombotic activity, which may either propagate the existing clot or lead micro-embolization into small pulmonary arteries, worsening right ventricular failure.

Clinicians treating patients with PE do not currently have a practical method of determining the degree to which anticoagulation has arrested the process of clotting. The doses of anticoagulants necessary to treat PE are determined in large part by outcome measures in patients who are clinically stable. An assay is described below for fibrinopeptide B (FPB) and its metabolites, which are released into the circulation only during active thrombosis. This assay was used in an animal model to determine if pulmonary embolization itself accelerates the thrombotic activity of pre-existing deep vein thrombi.

Since the immunoassay for human FPB does not recognize canine FPB, the canine thrombosis model is modified so that both the pre-existing thrombi and the circulating fibrinogen are predominantly of human origin. Therefore, the dogs have their native fibrinogen inactivated to a substantial degree.

Materials

Maxisorp ELISA plates were obtained from Nunc (Naperville, Ill.). Synthetic human fibrinopeptide B and fibrinopeptide A (both 99% pure), canine fibrinogen (>60% clottable), bovine serum albumin (>98% pure), ancrod, and tranexamic acid were purchased from Sigma (St. Louis, Mo.). N-cysteinyl fibrinopeptide B (>90% pure) and des-arg fibrinopeptide B (>98% pure) were custom synthesized by Peninsula Laboratories (San Carlos, Calif.) and ImmunoDynamics (La Jolla, Calif.) respectively. Human fibrinogen (>95% clottable) and aprotinin were purchased from Calbiochem (La Jolla, Calif.). Affinity purified goat anti-rabbit IgG (Fc fragment specific, peroxidase-conjugated) was purchased from Jackson ImmunoResearch Laboratories (West Grove, Pa.). Maleimide-activated keyhole limpet hemocyanin and Freund's adjuvant (complete and incomplete) were purchased from Pierce (Rockford, Ill.). Topical thrombin (bovine) and unfractionated heparin (porcine) were obtained from Jones Pharma (St. Louis, Mo.) and Elkins-Sinn (Cherry Hill, N.J.), respectively. Propofol and halothane were obtained from Zeneca Pharmaceuticals (Wilmington, Del.) and Halocarbon Laboratories (River Edge, N.J.), respectively. All other chemicals were reagent grade or better.

Methods

FPB Antiserum

An immunoconjugate of human FPB was prepared by coupling 5 mg of N-cysteinyl-FPB to 10 mg of maleimide-activated keyhole limpet hemocyanin according to a protocol provided by Pierce Chemical Company. Polyclonal antiserum to FPB was raised in New Zealand White rabbits. Three rabbits each received a primary subcutaneous injection of immunoconjugate (one mg) in complete Freund's adjuvant followed by two subcutaneous booster injections (one mg each) in incomplete Freund's adjuvant) given at four week intervals. Rabbits were bled at two-week intervals starting two weeks after the primary injection. After allowing the blood to clot overnight at 4 C., antiserum was collected by centrifugation (2000×g, 10 min) and stored at −20 C. until analyzed. The FPB antibody titer of each antiserum was determined in a direct-binding ELISA. Briefly, microplate wells were coated with synthetic FPB and blocked with BSA. Wells were then incubated with serial dilutions of FPB antiserum followed by peroxidase-conjugated goat anti-rabbit IgG detecting antibody. Wells were developed with o-phenylenediamine (OPD) substrate solution, and the absorbance (490 nm) of each well was measure in a microplate reader (Molecular Devices, Sunnyvale, Calif.). The antibody titer was arbitrarily defined as the antiserum dilution resulting in an absorbance of 1.0. The antiserum yielding the highest titer (1:2500) was used in the FPB assay described below.

FPB Assay

A competitive ELISA was developed for determination of the FPB concentration in plasma and urine ultrafiltrates. Unless otherwise noted, all steps were performed at room temperature, and the microplates were washed three times in between each step with 0.02 M $NaH_2PO_4$, 0.15 M NaCl, 1 mM EDTA, pH 7.4 (PNE) containing 0.1% tween-20. Microplate wells were first coated with synthetic FPB (2 µg/ml in 0.2 M $NaHCO_3$, 100 µl/well) overnight at 4 C., and then "blocked" with 1% BSA in PNE (PNEA) for one hour. Meanwhile, 20 µl of ultrafiltered samples and synthetic FPB standards (1.56–100 ng/ml) were pre-incubated separately with 200 µl of FPB antiserum (1:2500) in polypropylene microfuge tubes for one hour. Dilutions of the FPB standard and antiserum were prepared in dilution buffer (PNEA containing 0.1% tween-20). At the end of the pre-incubation period, 100 µl of each mixture were applied to duplicate FPB-coated wells and incubated for one hour. After washing, 100 µl of peroxidase-conjugated goat anti-rabbit IgG detecting antibody (1:5000 in dilution buffer) were added to each well and incubated for one hour. After a final wash, each well was developed with 100 µl of OPD substrate solution for exactly five minutes. The reaction was stopped by addition of an equal volume of 3 N $H_2SO_4$, and the absorbance (490 nm) of each well was measured in a microplate reader. The concentration of FPB in the samples was interpolated from a standard curve obtained by plotting the FPB concentration of each standard versus the corresponding absorbance. If sample values exceeded the upper limit of the standard curve, those samples were re-tested after appropriate dilution with dilution buffer. The intra- and inter-assay coefficients of variation for the FPB assay were 14.1% and 5.0%, respectively. The competitive ELISA was also used to assess the cross-reactivity of the FPB antiserum with human fibrinogen, fibrinopeptide A (FPA), des-arg FPB, and canine FPB.

Fibrinogen Assay

Fibrinogen levels in plasma were determined using a commercial kit (Sigma, St. Louis, Mo.). Briefly, 25 µl of sample (or standard) diluted in buffer were mixed with 50 µl of thrombin solution provided with the kit, and the clotting time was recorded. The clotting time was taken as the first appearance of a fibrin "string" from repeated dipping of a wooden applicator stick into the sample (or standard) and thrombin mixture. All assays were performed in triplicate. The fibrinogen concentration of each sample was determined by interpolation from a standard curve obtained by plotting log (fibrinogen concentration) versus log (clotting time). The fibrinogen concentration of samples containing heparin, or samples with low fibrinogen (less than 20 mg/dL) could not be determined due to an inability to form a fibrin clot in the assay.

Fibrinogen Replacement and Thrombosis Model

Eight healthy male mongrel dogs (20–24 kg) were used in the study. Each animal was anesthetized with intravenous Propofol (6–10 mg/kg), intubated, and mechanically ventilated. Anesthesia was then maintained throughout the study period with Halothane (1–2% in room air). Native canine fibrinogen was depleted by intravenous infusion of ancrod (2–3 u/kg) over a four-hour period. Each animal was allowed to recover from anesthesia and returned to quarters. Two days later, each animal was anesthetized, intubated and ventilated as before, and a Foley catheter was placed for urine collection. A catheter was placed in the dorsalis pedis artery for continuous blood pressure monitoring. Normal saline (0.9% NaCl) was administered intravenously to maintain urinary output at approximately 50 mL/h. Each animal was then transfused with six grams of purified human fibrinogen (dissolved in 250 mL of normal saline) over a 90-minute period. Following fibrinogen replacement, tranexamic acid was administered intravenously (110 mg/kg every six hours) to inhibit fibrinolysis. Cut-downs were performed bilaterally on the saphenous veins for placement of special double-balloon catheters, which were subsequently advanced under fluoroscopy into the right and left femoral veins. After balloon inflation, which created a sealed intra-vascular chamber, thrombosis was induced by injecting bovine thrombin (200 units) through a small port in the catheter between the inflated balloons. During a four-hour clot-aging period, the balloons were partially deflated to allow for restoration of blood flow and clot propagation. After the clot-aging period, pulmonary emboli were created by passive motion of one of the legs containing a femoral thrombus (see below).

Allocation of subjects

Three of the eight animals were arbitrarily selected to receive intravenous heparin (300 units/kg bolus followed by 90 units/kg/hr infusion) one hour prior to embolization of the femoral thrombus. At the conclusion of the study (five hours after embolization), each animal was given a bolus intravenous injection of heparin (3000 units) to prevent post-mortem blood coagulation, followed by intravenous nembutal (120 mg/kg) to induce cardiac arrest. An autopsy was carefully performed to determine the precise location of all clots. Finally, all femoral vein thrombi and pulmonary emboli were collected separately and weighed. The protocol was approved by the University of California, San Diego Animal Subjects Committee. Care and handling of experimental animals conformed to the standards established by the University of California, San Diego Department of Veterinary Services, which are in compliance with Federal recommendations.

Sample Collection and Processing

Blood samples (4.5 mL) were drawn at various times during the study and added to vacutainer tubes containing 0.5 mL of 0.129 M buffered sodium citrate with protease inhibitors (500 units each of aprotinin and heparin). Protease inhibitors were omitted from blood samples used for fibrinogen assay. Plasma was obtained by centrifugation at 2500×g for 10 minutes (4 C.). Plasma for fibrinopeptide B (FPB) assay was diluted with an equal volume of 0.9% (w/v) NaCl and subjected to ultrafiltration using Ultrafree (Biomax-100) centrifugal filter devices (Millipore, Bedford, Mich.) according to the manufacturer's recommendations, and the ultrafiltrate was saved for analysis. Urine was collected in 60-minute intervals throughout the study, starting with the onset of human fibrinogen transfusion. The volume of urine collected during each 60-minute time interval was recorded, and a sample (4.5 mL) for FPB assay was added to a vacutainer tube containing sodium citrate with protease inhibitors, clarified by centrifugation (2500×g, 10 minutes, 4 C.), and then subjected to ultrafiltration as described above. All samples were stored at −70 C. until analyzed.

Statistics

Data are presented as mean±standard error of mean (SEM) unless otherwise noted. Group comparisons were performed on log transformation of raw data using the unpaired t test (two-sided). Differences between means were deemed significant for $p<0.05$.

Results

Specificity of the FPB Antiserum

Figure 1B:
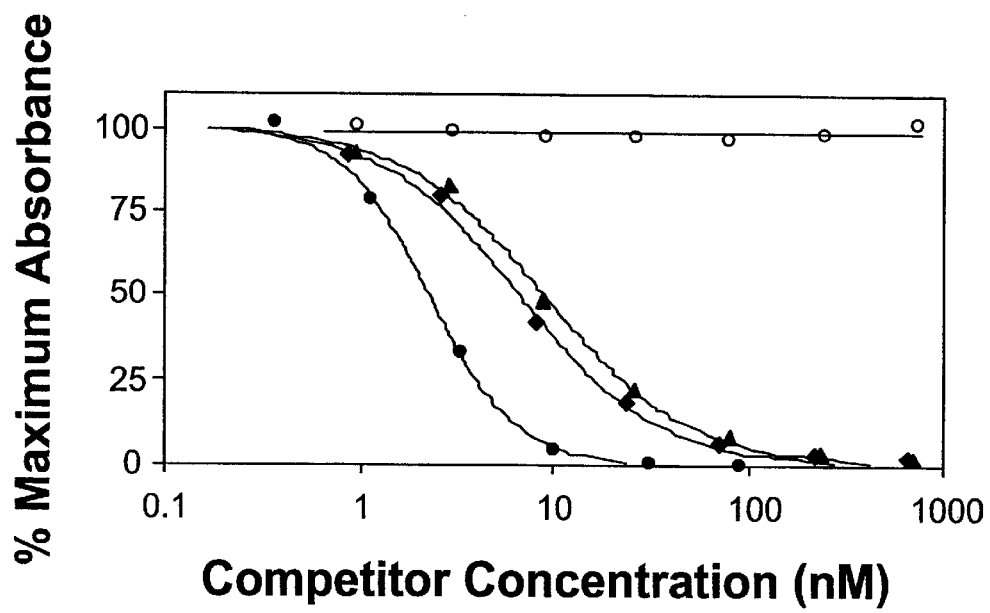

The specificity of the FPB antiserum was assessed in the competitive ELISA described above. As shown in FIG. 1A, native human FPB in solution was an effective competitive inhibitor of antibody binding to surface-bound synthetic human FPB. In contrast, native canine FPB in solution did not compete for antibody binding to surface-bound synthetic human FPB. Competitive ELISA was also used to assess the cross-reactivity of the FPB antiserum with human fibrinogen as well as several synthetic human fibrinopeptides. As shown in FIG. 1B, the competition curves for FPB and des-arg FPB were nearly identical. The cross-reactivity of des-arg FPB, defined as $IC_{50}$ of FPB (6.7 nM) divided by $IC_{50}$ of des-arg FPB (8.9 nM) times 100, was 75%. Thus, the FPB assay is sensitive to both FPB and its primary metabolite, des-arg FPB. Although FPA exhibited essentially no cross-reactivity (<0.1%), parent fibrinogen showed significant cross-reaction. The $IC_{50}$ of fibrinogen (2.3 nM) was about one-half the $IC_{50}$ of FPB, not unexpected since each fibrinogen molecule harbors two potentially cross-reacting FPB sequences. Cross-reacting fibrinogen molecules (340,000 kD) were effectively removed from study samples by centrifugal ultrafiltration with Biomax-100 membranes (100,000 kD cut-off) during sample processing (data not shown).

Fibrinogen Replacement

Because the FPB antiserum did not cross-react with canine FPB in the FPB assay, it was necessary to replace canine with human fibrinogen in the thrombosis model. This was accomplished by pre-treating each animal with ancrod, which effectively depleted autologous fibrinogen from the circulation. Plasma fibrinogen levels were determined before and after treatment with ancrod, and then again before and at various times after transfusion with purified human fibrinogen. During a two-day rest period in between ancrod treatment and heterologous fibrinogen transfusion, ancrod was cleared from the circulation (data not shown) and fibrinogen levels remained below the limit of detection. Fibrinogen levels after ancrod treatment and before replacement with human fibrinogen were below the limit of detection (20 mg/dL) in all animals. Following transfusion with purified human fibrinogen, the plasma fibrinogen level was restored to approximately 400 mg/dL and remained within normal limits (200–400 mg/dL) throughout the remainder of the study period.

Clot Characteristics

A femoral thrombus and pulmonary embolus was recovered from each animal at autopsy. Emboli were sometimes lodged in multiple lobar and/or segmental pulmonary arteries. Clots ranged in weight from 0.37–2.50 grams for thrombi and 0.29–0.78 grams for emboli (combined weight of all pieces). The mean±SEM clot weights for thrombi (0.82±0.26 g) and emboli 0.54±0.06 g) were not significantly different (p=0.31).

Plasma FPB Levels During Thromboembolism

Figure 2:
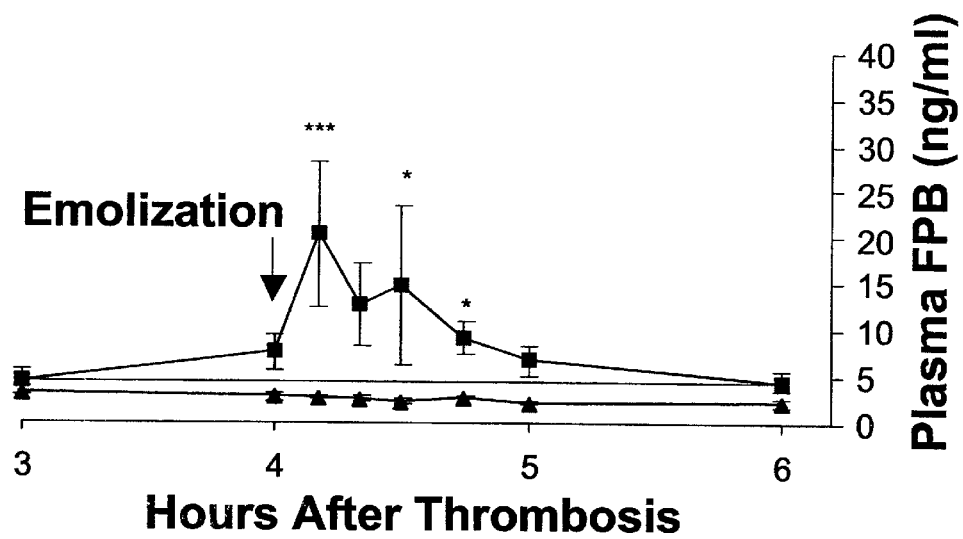
FIG. 2. Plasma FPB Levels During Thromboembolism. Plasma FPB levels were measured in all eight experimental animals (diamonds) before and at the indicated times after induction of bilateral femoral vein thrombosis. Four hours after thrombosis, one of the femoral clots in each animal was embolized to the lungs. One hour before embolization, heparin therapy was initiated in three of the animals (triangles). The other five animals (squares) did not receive heparin before embolization. Data are presented as the mean±SEM FPB level for each group of animals. $^*p<0.05$, $^{}p<0.01$, $^{*}p<0.005$ compared to baseline (time=0) level.
Figure 3:
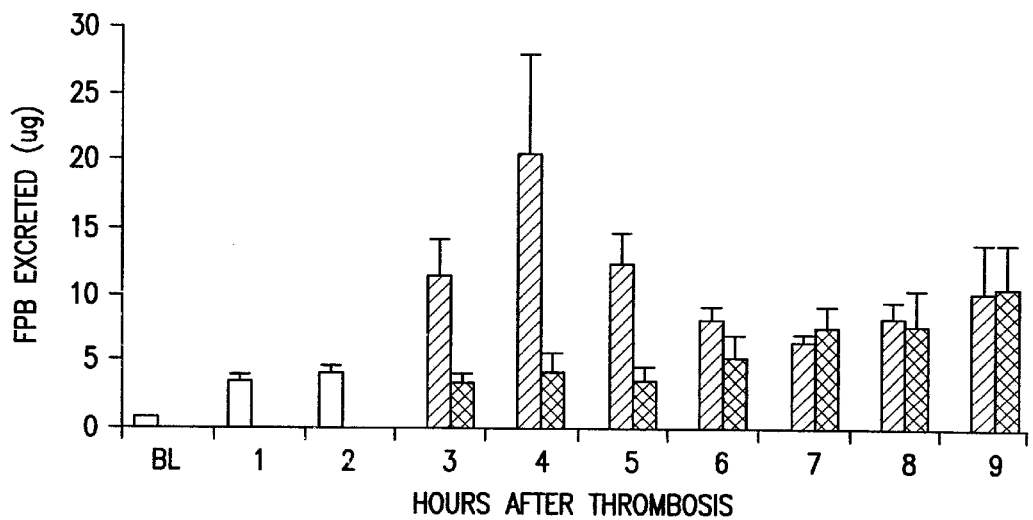
FIG. 3. Total Urinary FPB During Thromboembolism. FPB levels were measured in hourly urine collections before and after induction of bilateral femoral vein thrombosis. The baseline sample (BL) was taken from the hourly collection just prior to insertion of the double balloon catheters used for induction of thrombosis. Total urinary excretion of FPB for each time interval was determined by multiplying the FPB concentration in the urine by the total volume collected during the hourly interval. Four hours after thrombosis, one of the femoral clots in each animal was embolized to the lungs. One hour before embolization, heparin therapy was initiated in three of the animals. Data are presented as the mean±SEM urinary FPB for each group of animals. White bar: all animals (n=8). Grey bar: animals not treated with heparin prior to embolization (n=5). Black bar: animals treated with heparin prior to embolization (n=3). Total urinary FPB was significantly elevated compared to baseline ($p<0.05$) at all times after induction of thrombosis in all groups of animals.

FPB levels in plasma were measured before, and at various times after induction of femoral vein thrombosis. As shown in FIG. 3, the mean±SEM plasma level rose sharply from baseline (3.7±1.1 ng/mL) to a peak level of 25.4±8.9 ng/mL (p<0.005) ten minutes after induction of thrombosis. FPB levels then fell but remained significantly elevated (p<0.05) for the first hour after thrombosis before returning to near baseline. Four hours from induction of thrombosis, one of the two femoral clots in each animal was embolized. One hour prior to embolization, three of the animals were treated with intravenous heparin as described in the Methods section. After embolization, FPB again rose sharply to a peak level of 20.2±7.7 ng/ml, and then returned to baseline within one to two hours. However, the rise in FPB following embolization was completely suppressed in the animals treated with heparin prior to embolization (FIG. 2).

Urinary FPB Levels During Thromboembolism

Urine was collected hourly from each animal before and after induction of femoral vein thrombosis. Total FPB excreted in the urine during each time interval is presented in FIG. 3. The mean±SEM total urinary FPB for all animals was significantly elevated (3.3±0.7 $\mu$g) from baseline (0.5±0.1 $\mu$g) within one hour of thrombosis (p<0.001) and remained significantly elevated throughout the study period. The initial peak of urinary FPB (20.3±7.3 $\mu$g) occurred four hours after induction of thrombosis as opposed to the initial peak of plasma FPB, which occurred ten minutes after induction of thrombosis. The initial peak of urinary FPB was suppressed in animals treated with heparin prior to embolization. Total urinary FPB was on the rise again in all animals during the last time interval of the study (five hours after embolization). Besides total FPB, the concentration of FPB in each hourly urine collection following induction of thrombosis was also significantly elevated compared to baseline for each group of animals (data not shown).
Conclusions Plasma FPB rapidly rises during active thrombosis, but is also rapidly cleared from the circulation. The peptide appears in the urine after a delay of one to several hours from the onset of thrombosis and remains elevated even if thrombus propagation is suspended by systemic anticoagulants. Thus, urine FPB levels can provide an excellent indication of recent thrombotic activity even when the thrombus propogation is no longer occuring at the time the patient is tested or seeks medical assistance. It was also noted that pulmonary embolization itself causes an acceleration of thrombosis, which can be completely inhibited with heparin. Therefore, DVT patients with a high risk of embolization should be promptly anticoagulated.

EXAMPLE 4
Elevation of FPB in Clinical Samples Taken from Patients with DVT and PE The objectives of this experiment was to determine if plasma and urine levels of FPB (using the newly created ELISA assay) are higher in patients with acute pulmonary embolism or deep venous thrombosis than they are in normal volunteers and in those with other medical conditions.

VTE commonly occurs in the setting of other medical illnesses (Goldhaber et al. 1983, Hirsch et al. 1995), and it would be helpful to include these complex patients in the current project. Unfortunately, many medical conditions involve diffuse fibrin polymerization at sites of inflammation, which may alter the plasma levels of thrombosis markers. Therefore, the next step in the project is to determine whether $FPB_{tot}$ levels can distinguish patients with VTE from patients with other illness.

A clinical study was performed at UCSD testing urinary FPB levels in patients suspected of having DVT and/or PE. The results demonstrated that FPB levels increased sufficiently during DVT and PE to distinguish patients with thrombosis from those with other medical conditions (Eckhardt et al. 1981)
Methods Consecutive inpatients at the UCSD medical center referred by their treating physicians to the Acute Venous Thrombo-embolism Service, and suspected of having either a DVT or PE were asked to participate in the study. Informed consent was obtained by one of the investigators.

Upon entry into the study, blood and urine samples were collected from the patient (prior to the initiation of systemic anticoagulation, if possible). These samples were processed for ex-vivo analysis with the newly created FPB ELISA assay.

The subjects completed diagnostic workup for venous thromboembolic disease (as indicated clinically). Without knowledge of the laboratory test results, the PI reviewed the objective tests used to confirm or refute the diagnoses of DVT (lower extremity compression ultrasound exams, venograms) and PE (ventilation/perfusion scans, contrast-enhanced helical CT scans, pulmonary angiograms). According to accepted criteria, the patients were classified as: 1) VTE positive—thromboembolic disease confirmed by objective testing; 2) VTE negative—thromboembolic disease refuted; or 3) VTE indefinite—definitive testing not completed.

Figure 4:
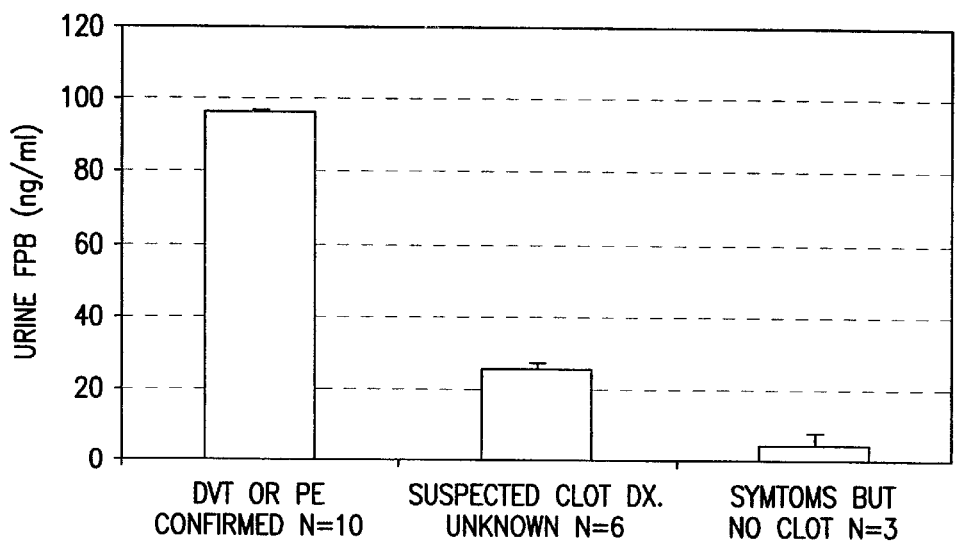
FIG. 4 (example 4). Urine FPB levels were markedly higher in patients with DVT (96+/−41) ng/ml) than in patients without DVT (2.7+/−1.9 ng/ml) and in healthy control subjects (2.15+/−1.9 ng/ml). (All values expressed as mean+/−SEM.)

In those patients who received therapy for VTE, a second blood and urine sample was obtained once adequate levels of anticoagulation have been achieved (assessed by clinical parameters). Again, these samples were processed for ex-vivo analysis with the FPB ELISA assay.
Results The urine FPB levels were markedly higher in the patients with DVT than in patients without DVT and in controls (FIG. 4). Ten patients in whom the diagnosis was conformed by objective testing had mean (+/−SEM) levels of FBP in the urine of 96 (+/−41) ng/ml. Three patients in whom the diagnosis was refuted had urinary FPB levels of 2.7 (+/−1.9) ng/ml. The mean (+/−SEM) urinary FPB level in nine healthy control patients was 2.15 (+/−1.9) ng/ml.

In these experiments, there was no difference in plasma $FPB_{tot}$ levels between normal volunteers and patients with DVTs (results not shown) despite the strong dependence observed with urine FPB levels. Although the few patients with pulmonary emboli tended to have higher plasma levels of $FPB_{tot}$, the differences were not great and the population tested in these preliminary experiments was small. Therefore, although the invention includes FPB tests for both plasma and urine, the focus for the next examples was on the determination of FPB levels in the urine.

It was noted that we observed excellent correlation of FPB levels in urine with the presence or absence of DVT even though no correction was made for urine volume or rates of glomerular filtration. In some applications it is beneficial to also measure a marker (e.g., creatinine, protein, albumin) in the urine that is indicative of urine volume or rates of glomular filtration. The concentration of this marker can be used to normalize the measured concentration of FPB so as to account for these effects.
Conclusions Thus, urine FPB levels are much higher in patients with venous thromboembolic disease than they are in other patients.

EXAMPLE 5

Measurement of FPB in the Plasma and Urine of Hospitalized Patients at Risk of DVT/PE.
Objective To further delineate the specificity of FPB for acute thrombosis, FPB plasma/urine levels are measured in hospitalized patients with a variety of other medical and surgical conditions, in whom the diagnosis of venous thromboembolic disease is not suspected (and not suggested by screening tests).
Methods Enrollment. Consecutive inpatients at UCSD Medical Center (n=765) in whom compression stockings are requested for VTE prophylaxis, and in whom the attending physicians give permission for entry were considered candidates for the study. Informed consent is obtained by one of the investigators. The investigators perform an initial screen for DVT (see below). Exclusion criteria include refusal of consent, DVT on initial CUS, arterial insufficiency, contact allergy to the cuff material, injury to the lower extremity precluding cuff use, use of IPC devices for greater than 12 hours during the current admission and previous episodes of VTE. Plasma and Urine FPB Levels are measured in each patient as follows: At each time point described below, blood samples (20 ml by fresh venupuncture) and urine samples (20–40 ml) are collected into tubes containing anticoagulants. Plasma and urine are ultrafiltered to remove fibrinogen and tested for fibrinopeptide B. The levels are compared to the results of the results of the following anatomical screening tests for DVT and PE.

Time Points for Outcome Measurement. Patients are screened for VTE at the following time points: upon entry into the study, two weeks after application of the venous compression device, upon discontinuation of the device and one week after discontinuation of the device. In those cases where the patients have been discharged earlier than one week after discontinuation of the devices, they are offered a small monetary incentive for returning for a final examination. The details of the screening are discussed below.

Outcome—DVT. Compression ultrasonography (CUS) is used to confirm the presence of DVT in symptomatic patients and to screen for DVT in asymptomatic patients. The strength of this approach is that the specificity of CUS for asymptomatic DVT is 97%, roughly equal to the specificity in symptomatic patients. Therefore, a positive test can be relied upon.

At each time point, patients are interviewed, examined and CUS is performed. If no signs or symptoms of DVT are disclosed, and the CUS is negative, no further work-up is performed. If CUS discloses non-compressible proximal LE veins (popliteal and above), the patient is considered to have a DVT, regardless of symptoms. If signs or symptoms of DVT are present, and the initial the CUS is negative, it is repeated on day two and seven. If any of the serial CUS exams disclose non-compressible LE veins, the patient is considered to have a DVT. If none are positive, the patient was considered to be free of DVT.

Patients with signs or symptoms DVT upon entry into the study in whom the first series of CUS studies disclose DVT are assumed to have had DVT prior to application of IPC. These patients are dropped from the study and excluded from further analysis.

Outcome—PE. At each time point, patients are interviewed and examined. If no signs or symptoms of PE are disclosed, no further work-up is performed. If a PE is clinically suspected, the patients attending physician is notified. It is the standard of care at UCSD Medical Center to perform a work-up that follows ATS guidelines. Briefly, a ventilation/perfusion (V/Q) scan is performed, if possible. Normal V/Q scans are accepted as ruling out PE. Scans disclosing two or more segmental or larger perfusion defects unmatched by ventilation defects ("high probability" scans) are accepted as diagnostic of PE. All other scans are considered non-diagnostic. Patients with non-diagnostic V/Q scans received pulmonary angiography. Although the investigators recommend that the work-up for PE follows these guidelines, diagnostic tests are ordered as indicated by the patients' attending physicians.

The attending physician of any patient diagnosed with DVT or PE is notified of the results of the diagnostic tests. Treatment is at the discretion of the attending physician, although a consultation from the Acute Venous Thrombo-Embolism service is usually offered.

Results

Figure 5:
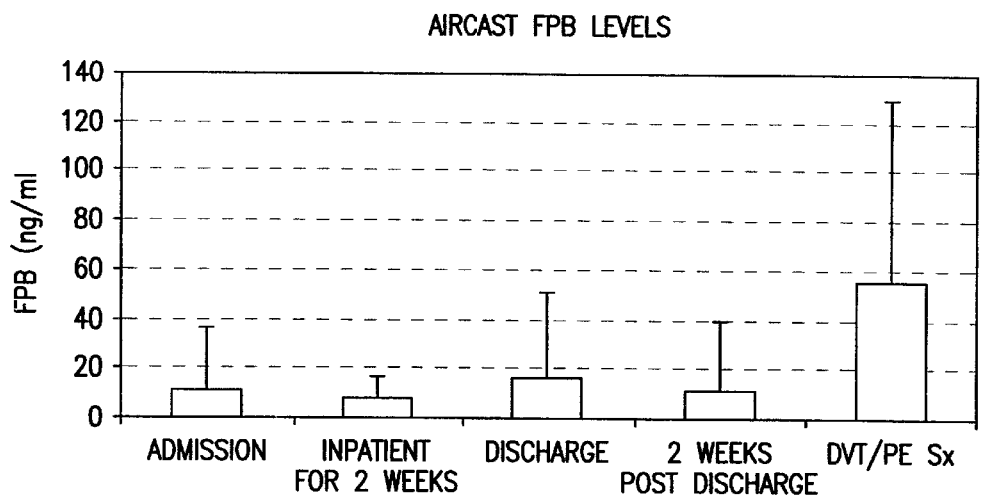
FIG. 5 (example 5) The mean (+/−SD) levels of FBP in the urine of 209 patients without DVT, being admitted to the hospital for various reasons, were 11.6 (+/−25.4) ng/ml (FIG. 5). At the time of discharge (after hospitalization for a least 48 hours), the urine FPB levels in those without DVT were 16.5 (+/−34.3). These levels are markedly below those observed in patients with DVT or PE (see FIG. 4).

The mean (+/−SD) levels of FBP in the urine of 209 patients without DVT, being admitted to the hospital for various reasons, were 11.6 (+/−25.4) ng/ml (FIG. 5). At the time of discharge (after hospitalization for a least 48 hours), the urine FPB levels in those without DVT were 16.5 (+/−34.3).

Conclusions

These results indicate that elevated levels of urinary FPB are uncommon in hospitalized patients, which is not the case for the plasma D-dimer test. The specificity of the FPB is therefore higher than for other clinically available markers for thrombosis, such as the D-dimer.

EXAMPLE 6

FPB Levels During Treatment

The objective of this experiment was to determine if urinary or plasma FPB levels, measured during anticoagulation with "therapeutic doses" of heparin, are reduced relative to the pre-treatment levels in VTE patients.

The validity of $FPB_{tot}$ for following anticoagulation efficacy is tested by determining whether urine levels (or the plasma levels described above) reliably fall as VTE is treated with large doses of heparin.

Consecutive patients referred to the VTE service in whom the diagnosis of DVT and/or PE is confirmed (based on the criteria described above) are enrolled. Prior to therapy, blood and urine samples are collected for measurement of $FPB_{tot}$ (and other FPB measurements described above). Patients are then be treated with intravenous heparin (80 units/kg bolus, 18 units/kg/hr infusion), with the dose adjusted per protocol to keep aPTT 1.5–2.5 times the control values. As soon as steady-state "therapeutic doses" of heparin are maintained, blood and urine are collected again and the same parameters are measured. In addition, plasma aPTT, anti-Xa and anti-thrombin measurements are made as previously described (Morris et al. 1998).

For each patient, the difference between urinary and plasma $FPB_{tot}$ levels, measured before and after anticoagulation, is recorded. The mean reduction in $FPB_{tot}$ levels after anticoagulation is calculated. The required sample size is estimated based on the preliminary data described below: The mean (+/−SD) decrease in urinary $FPB_{tot}$ during anticoagulation was 60 ng/ml (+/−85.7 ng/ml). Assuming similar standard deviations for the VTE patients to be studied, thirty-seven pairs of samples are required in order to detect a 50% decrease in the levels after anticoagulation, with an alpha of 0.01 and a power of 95%.

Preliminary Results

Urinary levels of FPB significantly decreased during anticoagulation in all but one patient (figure). The sole patient in whom urinary FPB increased had sustained a crush injury to his leg and required major surgery on the day that his repeat samples were obtained. More importantly, his heparin dose, as estimated by his aPTT measurements, had not achieved therapeutic range during the time interval between his first and second tests. In fact this patient also demonstrated larger elevations in his plasma FPB on his second day of sampling than on his first day (results not shown).

Discussion

This portion of the study suggests that urine levels of FPB have the unique property of decreasing as patients with VTE are anticoagulated. After further development of the test (and perhaps development of variations in the FPB plasma test—described above) they may be used as valid estimates of the short-term effectiveness of anticoagulation. These markers may represent the first test of actual anti-thrombotic effectiveness applicable in the clinical setting.

All publications and patents are herein incorporated by reference to the same extent as if each individual publication or patent application was specifically and individually indicated to be incorporated by reference. It will be apparent to one of ordinary skill in the art that many changes and modifications can be made in the invention without departing from the scope of the appended claims.

BIBLIOGRAPHY

U.S. Pat. Nos. 6,066,448, 6,078,782, 5,731,147, 5,876,947.

Becker D M, Philbrick J T, Bachhuber T L, Humphries J E: D-dimer testing and acute venous thromboembolism. A shortcut to accurate diagnosis? *Arch Intern Med* 156:939–946 (1996).

Bell, W. R. J., Defibrinogenating enzymes. *Drugs,* 54 Suppl 3:18–30 (1997).

Bilezikian, S B, Nossel H L, Butler V P and Canfield R E, "Radioimmunoassay of human fibrinopeptide B and kinetics of fibrinopeptide cleavage by different enzymes," *J. Clinical Investigation* 56:438–445 (1975).

Bini A, Callender S, Procyk R, Blomback B and Kudryk B J, "Flow and antibody binding properties of hydrated fibrins prepared from plasma, platelet rich plasma and whole blood," *Thrombosis Res* 76(2):145–156 (1994).

Bini A, Fenoglio J J Jr, Mesa-Tejada R, Kudryk B and Kaplan K L, "Identification and distribution of fibrinogen, fibrin, and fibrin(ogen) degradation products in atherosclerosis," *Arteriosclerosis* 9(1):111–121 (1989).

Bini A, Fenoglio J J Jr, Sobel J, Owen J, Fejgl M and Kaplan K L, "Immunochemical characterization of fibrinogen, fibrin I and fibrin II in human thrombi and atherosclerotic lesions," *Blood* 69(4):1038–1045 (1987).

Bini A, Itoh Y, Kudryk B J and Nagase H, "Degradation of cross-linked fibrin by matrix metalloproteinase 3 (stromelysin 1): Hydrolysis of γGly404-Ala405 peptide bond," *Biochemistry* 35(40):13056–13063 (1996).

Bini A and Kudryk B J, "Fibrin and its derivatives in the normal and diseased vessel wall," *Ann NY Acad Sci* 667:112–126.

Bini A, Mesa-Tejada R, Fenoglio J J Jr, Kudryk B and Kaplan K L, "Immunohistochemical characterization of fibrin(ogen)-related antigens in human tissues using monoclonal antibodies," *Laboratory Investigation* 60(6):814–821 (1989).

Bovil, E. G., McDonagh, J., Triplett, D. A., Arkin, C. F., Brand, J. T., Hayes, C. E., Kaczmarek, E., Long, T., Rock, W. A., Performance Characteristics of Fibrinogen Assays; Results of the College of American Pathologists Proficiency Testing Program 1988–1991. *Arch. Pathol. Lab. Med.,* 117:58–66 (1993).

Brandt, J. T., Triplette, D. A., Laboratory Monitoring of Heparin. Effect of Reagents and Instruments on the Activated Partial Thromboplastin Time. *Am. J. Clin. Pathol.,* 76:530–537 (1981).

Bounameaux H, Khabiri E, Huber O, Schneider P, Didier D, de Moerloose P, Reber G: Value of Liquid Crystal Contact Thermography and Plasma Level of D-Dimer for Screening of Deep Venous Thrombosis Following General Abdominal Surgery. *Thromb Haemost* 67:603–606 (1992).

Bounameaux H, Cirafici P, de Moerloose P, Schneider P, Slosman D, Reber G, Unger P F: Measurement of D-Dimer in Plasma as Diagnostic Aid in Suspected Pulmonary Embolism. *Lancet* 337:196–200 (1991).

Carrier, D., Caranobe, C., Boneu, B., A Comparison of the Antithrombotic Effects of Heparin and of Low Molecular Weight Heparins with Increasing Antifactor Xa/Antifactor IIa Ratio in the Rabbit. *British Journal of Hematology,* 83:622–626 (1993).

Carrier, D. Caranobe, C., Gabaig, A. M., Larroche, M., Boneu, B., Effects of Heparin, Dermatan Sulfate and of their Association on the Inhibition of Venous Thrombosis Growth in the Rabbit. *Thrombosis and Haemostasis,* 68:637–641 (1992).

Campbell, Monoclonal Antibody and Immunosensor Technology, Elsevier, Amsterdam. pp. 3–6, 20–23, 42–45 (1991).

Chung et al. Characterization of complementary deoxyribonucleic acid and genomic deoxyribonucleic acid for the β chain of human fibrinogen. *Biochemistry* 22:3244–3250 (1983).

Collen D and Lijnen H R, "Basic and clinical aspects of fibrinolysis and thrombolysis," *Blood* 78(12):3114–3124 (1991).

Dalen, J. E., Hirsh, J., American College of Chest Physicians and the National Heart, Lung and Blood Institute National Conference on Antithrombotic Therapy. *Arch. Intern. Med.,* 146:462–472 (1986).

Douketis, J. D., Kearon, C., Bates, S., Duku, E. K., Ginsberg, J. S., Risk of fatal pulmonary embolism in patients with treated venous thromboembolism. *JAMA,* 279:458–462 (1998).

Dyr J E, Blomback B, Hessel B, Komalik F: Conversion of fibrinogen to fibrin induced by preferential release of fibrinopeptide B. *Biochim.Biophys.Acta* 990:18–24 (1989).

Ebert R F, Bell W R: Assay of human fibrinopeptides by high-performance liquid chromatography. *Anal.Biochem.* 148:70–78 (1985).

Eckhardt T, Nossel H L, Hurlet-Jensen A, La Gamma K S, Owen J, Auerbach M: Measurement of desarginine fibrinopeptide B in human blood. *J Clin Invest* 67:809–816 (1981).

Fu Y and Grieninger G, "Fib.sub.420: A normal human variant of fibrinogen with two extended α chains," *Proc Natl Acad Sci* USA 91:2625–2628 (1994).

Fu Y, Weissbach L, Plant P W, Oddoux C, Cao Y, Liang T J, Roy S N, Redman C M and Grieninger G, "Carboxy-Termina-Extended variant of the human fibrinogen α subunit: a novel exon conferring marked homology to β and γ subunits," *Biochemistry* 31(48):11968–11972.

Gando, S., Tedo, I., Diagnostic and prognostic value of fibrinopeptides in patients with clinically suspected pulmonary embolism. *Thromb. Res.,* 75:195–202 (1994).

Gawoski, J. M., Arkin, C. F., Bovill, T., Brandt, J., Rock, W. A., Triplett, D. A., The Effects of Heparin on the Activated Partial Thromboplastin Time of the College of American Pathologists Survey of Specimens. *Arch. Pathol. Lab. Med.,* 111:785–790 (1987).

Ginsberg J S, Wells P S, Brill-Edwards P, Donovan D, Panju A, van Beek E J, Patel A: Application of a novel and rapid whole blood assay for D-dimer in patients with clinically suspected pulmonary embolism. *Thromb Haemost* 73:35–38 (1995).

Ginsberg J, Brill-Edwards P A, Donovan D: D-Dimer in Patients With Clinically Suspected Pulmonary Embolism. *Chest* 104:1679–1684 (1993).

Goldhaber S Z, Simons G R, Elliott C G, Haire W D, Toltzis R, Blacklow S C, Doolittle M H, Weinberg D S: Quantitative Plasma D-Dimer Levels Among Patients Undergoing Pulmonary Angiography for Suspected Pulmonary Embolism. *JAMA* 270:2819–2822 (1993).

Goldhaber, S. Z., Savage, D. D., Garrison, R. J., Castelli, W. P., Kannel, W. B., McNamara, P. M., Gherardi, G., Feinleib, M., Risk factors for pulmonary embolism. The Framingham Study. *Am. J. Med.,* 74:1023–1028 (1983).

Harlow, E., Lane, D., Immunizations, in Anonymous Antibodies: A Laboratory Manual. Cold Spring Harbor Laboratory (1998).

Harlow et al., Antibodies. A Laboratory Manual, Cold Spring Harbor Laboratory, Cold Spring Harbor. pp. 72–77, 600–612 (1998).

Higgins D L, Lewis S D, Shafer J A: Steady State Kinetic Parameters for the Thrombin-catalyzed Conversion of Human Fibrinogen to Fibrin. *J Biological Chemistry* 258:9276–9282 (1983).

Hirsch, D. R., Lee, T. H., Morrison, R. B., Carlson, W., Goldhaber, S. Z., Shortened hospitalization by means of adjusted-dose subcutaneous heparin for deep venous thrombosis. *Am. Heart J.,* 131:276–280 (1996).

Hirsch, D. R., Ingenito, E. P., Goldhaber, S. Z., Prevalence of deep venous thrombosis among patients in medical intensive care. *JAMA,* 274:335–337 (1995).

Hoellerich V L, Wigton R S: Diagnosing pulmonary embolism using clinical findings. *Arch Intern Med* 146:1699–1704 (1986).

Hull, R. D., Raskob, G. E., Brant, R. F., Pineo, G. F., Valentine, K. A., The importance of initial heparin treatment on long-term clinical outcomes of antithrombotic therapy. The emerging theme of delayed recurrence. *Arch. Intern. Med.,* 157:2317–2321 (1997).

Hull, R. D., Raskob, G. E., Hirsch, J. Jay, R. M., Leclerc, J. R., Geerts, W. H., Rosenbloom, D., Sackett, D. L., Anderson, C. Harrison, L., Gent, M., Continuous Intravenous Heparin Compared With Intermittent Subcutaneous Heparin In The Initial Treatment of Proximal-Vein Thrombosis. *NEJM,* 315:1109–1114 (1986).

Kinjoh et al., Production of a monoclonal antibody against rabbit fibrinopeptide B (FPB) for immunological assay of rabbit FPB. *Japanese Journal of Physiology* 44 (Supp. 1): S117, Abstract#272 (1994).

Koopman, M., Prandoni, P., Piovella, F., Treatment of Venous Thrombosis with Intravenous Unfractionated Heparin Administered in the Hospital as Compared with Subcutaneous Low-Molecular-Weight Heparin Administered at Home. *NEJM,* 334:682–687 (1996).

Koopman J, Haverkate F, Grimbergen J, Egbring R and Lord ST, "Fibrinogen Marburg: A homozygous case of dysfibrinogenemia, lacking amino acids Aα 461–610 (Lys 461 AAA Stop TAA)," *Blood* 80(8):1972–1979 (1992).

Kudryk B, Bini A, Procyk R, Matsueda G R and Shainoff J R, "Cross-linking of fibrinogen by tissue transglutaminase: Involvement of the C-termini of the Aα- and γ-chains in formation of Aαγ-dyads," *Thromb Haemostas* 69(6):1260 (1993).

Kudryk, B, Gidlund M, Rohoza A, Ahadi M, Coiffe D and Weitz J I, "Use of a synthetic homologue of human fibrinopeptide A for production of a monoclonal antibody specific for the free peptide," *Blood* 74(3):1036–1044 (1989).

Kudryk B J, Grossman Z D, McAfee J G and Rosebrough S F, "Monoclonal antibodies as probes for fibrin(ogen) proteolysis," Monoclonal Antibodies in Immunoscinitgraphy J-F. Chatal, ed. CRC Press, Boca Raton 365–398 (1989a).

Kudryk B, Robinson D, Netre C, Hessel B, Blomback M, and Blomback B, "Measurement in human blood of fibrinogen/fibrin fragments containing the Bβ15-42 sequence," *Thromb Res* 25:277–291 (1982).

Kudryk B, Rohoza A, Ahadi M, Chin J and Wiebe M E, "A monoclonal antibody with ability to distinguish between NH.sub.2 -terminal fragments derived from fibrinogen and fibrin," *Mol Immunol* 20:1191–1200 (1983).

Kudryk B, Rohoza A, Ahadi M, Chin J, and Wiebe M E, "Specificity of a monoclonal antibody for the $NH_2$-terminal region of fibrin," *Mol Immunol* 21:89–94 (1984).

Kudryk B, Rohoza A, Ahadi M, Gidlund M, Procyk R and Matsueda G R, *Thromb Haemostas* 65:898 (Abstract 714) (1991).

Levine, M., Gent, M., Hirsh, J. Leclerc, J., Anderson, D., Weitz, J., Ginsberg, J., Turpie, A. G., Demers, C., Kovacs, M., Geerts, W., Kassis, J., Desgjardins, L., Cusson, J., Cruickshank, M., Powers, P., Brien, W., Haley, S. Willan, A., A Comparison of Low-Molecular-Weight Heparin Administered Primarily at Home with Unfractionated Heparin Administered n the Hospital for Proximal Deep Vein Thrombosis. *NEJM,* 334:677–681 (1996).

Liu C Y, Sobel J H, Weitz J I, Kaplan K L, and Nossel H L, "Immunologic identification of the cleavage products from the A alpha- and B beta-chains in the early stages of plasmin digestion of fibrinogen," *Thromb Haemostas* 56(1):100–106 (1986).

Loike J D, Sodeik B, Cao L, Leucona S, Weitz J I, Detmers P A, Wright S D and Silverstein S C, "CD11c/CD18 on neutrophils recognizes a domain at the N terminus of the A-alpha chain of fibrinogen," *Proc Natl Acad Sci USA* 88:1044–1048 (1991).

Lopaciuk, S., Meissner, A. J., Filipecki, S., Zawilska, K., Sower, J., Ciesielski, L., Bielawiec, M., Glowinski, S., Czestochowska, E., Subcutaneous low molecular weight heparin versus subcutaneous unfractionated heparin in the treatment of deep vein thrombosis: a Polish multicenter trial. *Thromb. Haemost.,* 68:14–18 (1992).

Marsh, J. J., Konopka, R., Lang, I. M., Wang, H., Pedersen, C., Chiles, P., Reilly, C. F., Moser, K. M., Suppression of Thrombolysis in a Canine Model of Pulmonary Embolism. *Circulation,* 90:3091–3097 (1994).

Meyer, G., Brenot, F., Pacouret, G., Simonneau, G., Gillet, Juvin K., Charbonnier, B., Sors, H., Subcutaneous low-molecular-weight heparin fragmin versus intravenous unfractionated heparin in the treatment of acute non massive pulmonary embolism: an open randomized pilot study. *Thromb. Haemost,* 74:1432–1435 (1995).

Miller G J, Bauer K A, Barzegar S, Foley A J, Mitchell J P, Cooper J A, Rosenberg R D: The effects of quality and timing of venepuncture on markers of blood coagulation in healthy middle-aged men. *Thromb.Haemost.* 73:82–86 (1995).

Morris, T. A., Marsh, J. J., Konopka, R., Pedersen, C. A., Chiles, P. G., Moser, K. M., Comparison of Enoxaparin, Dalteparin and Unfractionated Heparin Using an In Vivo Marker for Propagating Canine Venous Thrombi. *Circulation* 1998; submitted.

Morris T A, Marsh J J, Fagnani R, Hagan M, Moser K M: Degree of Polymer Organization Decreases the Binding of a Monoclonal Antibody Raised Against the B-Chain Amino Terminus of Fibrin. *Thromb.Haemost.* 77:704–709 (1997a).

Morris T A, Marsh J J, Konopka R G, Pedersen C A, Chiles P G, Fagnani R, Hagan M, Moser K M: Antibodies Against the Fibrin B-Chain Amino Terminus Detect Active Canine Venous Thrombi. *Circulation* 96:3173–3179 (1997b).

Morris, T. A., Marsh, J. J., Konopka, R., Pedersen, C., Chiles, P., Moser, K. M., Anti-fibrin Antibodies Detect Deep Vein Thrombosis in a Canine Model. *Chest,* 104:24s (1993).

Moser, K. M., Spragg, R. G., Bender, F., Konopka, R., Hartman, M. T., Fedullo, P., Study of Factors That May Condition Scintigraphic Detection of Venous Thrombi and Pulmonary Emboli with Indium-111-Labeled Platelets. *J. Nuc. Med.,* 21:1051–1058 (1980).

National Heart, Lung and Blood Institute Urokinase Pulmonary Embolism Trial: Phase I Results. *JAMA,* 214:2163–2172 (1970).

Ng. A. S., Lewis, S. D., Shafer, J. A., Quantifying thrombin-catalyzed release of fibrinopeptides from fibrinogen using high-performance liquid chromatography. *Methods Enzymol.,* 222:341–358 (1993).

Owens et al., The genetic engineering of monoclonal antibodies. *J. Immunological Methods* 168: 149–165 (1994).

Plow E F and Edgington T S, "Surface markers of fibrinogen and its physiologic derivatives revealed by antibody probes," *Semin Thromb Haemostas* 8(1):36–56 (1982).

Procyk R, Kudryk B, Callender S, Blomback B, "Accessibility of epitopes on fibrin clots and fibrinogen gels," *Blood* 77: 1469–1475 (1991).

Raschke, R. A., Reilly, B. M., Guidry, J. R., Fontana, J. R., Srinivas, S., The Weight-based Heparin Dosing Nomogram Compared With a "Standard Care" Nomogram: A Randomized Controlled Trial. *Ann. Intern. Med.,* 119:874–881 (1993).

Reber G, Vissac A M, de Moerloose P, Bounameaux H, Amiral J: A new, semi-quantitative and individual ELISA for rapid measurement of plasma D-dimer in patients suspected of pulmonary embolism. *Blood Coagul Fibrinolysis* 6:460–463 (1995).

Russel, D., Hull, M. B., Subcutaneous Low-Molecular-Weight Heparin Compared With Continuous Intravenous Heparin In The Treatment of Proximal-Vein thrombosis. *NEJM,* 326:975–982 (1992).

Singer I I, Kawka D W, Bayne E K, Donatelli S A, Weidner J R, Williams H R, Ayala J M, Mumford R A, Lark M W, Glant T T, Nabozny G H and David C S, "VDIPEN, A metalloproteinase-generated neoepitope, is induced and immunolocalized in articular cartilage during inflammatory arthritis," *J Clinical Investigation* 95:2178–2186 (1995).

Southan C, Thompson E, Lane D A: Direct analysis of plasma fibrinogen-derived fibrinopeptides by high-performance liquid chromatography: investigation of nine congenital fibrinogen abnormalities. *Br.J Haematol.* 65:469–473 (1987).

Southan C, Thompson E, Lane D A: Direct analysis of plasma fibrinogen-derived fibrinopeptides by high-performance liquid chromatography. *Thromb.Res.* 43:195–204 (1986).

Tapson V F, Carroll B A, Davidson B L, Elliott C G, Fedullo P F, Hales C A, Hull R D, Hyers T M, Leeper K V, Morris T A, Moser K M, Raskob G E, Sostman H D, Thompson B T: American Thoracic Society Position Paper: The Diagnostic Approach to Acute Venous Thromboembolism. *American Journal of Respiratory and Critical Care Medicine* (1999, in press)

Tietz, Textbook of Clinical Chemistry, Burtis, C. Ashword, E. R., Eds., W B Saunders, Phaildelphia (1994).

Valenzuela R, Shainoff J R, DiBello P M, Urbanic D A, Anderson J M, Matsueda G R and Kudryk B J, "Immunoelectrophoretic and immunohistochemical characterizations of fibrinogen derivatives in atherosclerotic aortic intimas and vascular prosthesis pseudo-intimas," *Amer J Pathol* 141(4):861–880 (1992).

van Beek E J, Schenk B E, Michel B C, van den Ende B, Brandjes D P, van der Heide Y T, Bossuyt P M, Beuller H R: The role of plasma D-dimers concentration in the exclusion of pulmonary embolism [published erratum appears in Br J Haematol *Br J Haematol* 92:725–732 (1996)

van den Besselaar, A. M., Meeuwisse-Braun, J., Bertina, R. M., Monitoring heparin therapy: relationships between the activated partial thromboplastin time and heparin assays based on ex-vivo heparin samples. *Thromb. Haemost,* 63:16–23 (1990).

van Hulsteijn H, Brieet E, Koch C, Hermans J, Bertina R: Diagnostic value of fibrinopeptide A and beta-thromboglobulin in acute deep venous thrombosis and pulmonary embolism. *Acta Med Scand* 211:323–330 (1982).

Verstraete, M., Direct thrombin inhibitors: appraisal of the antithrombotic/hemorrhagic balance. *Thromb. Haemost,* 78:357–363 (1997).

Walenga, J. M., Jeske, W. P. Bara, L., Samama, M. M., Fareed, J., Biochemical and pharmacologic rationale for the development of a synthetic heparin pentasaccharide. *Thromb. Res.,* 86:1–36 (1997).

Weissbach L and Grieninger G, "Bipartite mRNA for chicken α-fibrinogen potentially encodes an amino acid sequence homologous to β- and γ-fibrinogens," *Proc Natl Acad Sci* USA 87:5198–5202 (1990).

Wilner et al., Immunochemical analysis of rqabbit antihuman fibrinopeptide B antibodies. *Biochemistry* 18:5078–5082 (1979).

Yung, G. L., Marsh, J. J., Berstein, R. J., Hirsh, A. M., Channick, R. N., Moser, K. M., Fibrinopeptide A Levels in Primary Pulmonary Hypertension. *American Journal of Respiratory and Critical Care Medicine,* 157:A592 (Abstract) (1998).

What is claimed is:

1. A method for detecting thrombotic or thromboembolic diseases in a patient comprising detecting a presence or amount of Fibrinopeptide B (FPB) and/or des-arginine FPB peptides in a sample of urine from the patient to determine whether the patient has thrombotic or thromboembolic disease.

2. The method of claim 1, wherein detecting the presence or amount of FPB peptide comprises conducting an immunoassay for FPB peptides.

3. The method of claim 1, further comprising measuring an indicator of urine volume or rate of glomerular filtration.

4. The method of claim 1, further comprising determining if the FPB peptide in the sample is present at a concentration of greater than 50 ng/mL.

5. The method of claim 1, further comprising determining if the FPB peptide in the sample is present at a concentration significantly greater than in a normal population.

6. A method of monitoring treatment of thrombotic or thromboembolic diseases in a patient comprising measuring a Fibrinopeptide B (FPB) and/or des-arginine FPB peptides level in a sample of urine from the patient and determining the level is significantly greater than in a normal population to determine whether the patient has thrombotic or thromboembolic disease.

7. A method for monitoring treatment of thrombotic or thromboembolic disease caused by a thrombosis or embolism in a patient comprising:
   (a) detecting an amount of Fibrinopeptide B (FPB) peptide present in a sample of urine obtained from the patient at a first time;
   (b) detecting an amount of FPB peptide present in a second sample of urine obtained from the patient at a second later time; and
   (c) comparing the amounts determined in steps (a) and (b) to determine whether the thrombosis or embolism is diminishing in size.

8. A diagnostic method for detecting thrombotic or thromboembolic disease in a patient comprising:

(a) contacting a urine sample from the patient, the sample suspected of containing a presence or amount of fibrinopeptide B (FPB) peptide and/or des-arginine FPB peptide, with an amount of detection agent specific for FPB and/or des-arginine FPB peptides to form an FPB: detection agent complex; and (b) detecting the presence or amount of FPB and/or des-arginine FPB peptides in the sample to determine whether the patient has thrombotic or thromboembolic disease.

9. A diagnostic method for monitoring treatment of thrombotic or thromboembolic disease in a patient comprising:

(a) contacting a urine sample suspected of containing fibrinopeptide B (FFB) peptide and/or des-arginine FPB peptide with an amount of detection agent specific for FPB and/or des-arginine FPB peptides to form an FPB:detection agent complex, wherein the sample is from a patient undergoing treatment for thrombotic or thromboembolic disease; and (b) detecting a presence or amount of FPB and/or des-arginine FPB peptides in the sample to monitor changes in the presence or amount of FPB and/or des-arginine FPB peptides in the patient to monitor treatment of the patient for thrombotic or thromboembolic disease.

10. The method of claim 8, wherein the detection agent is a monoclonal antibody.

11. The method of claim 8, wherein the detection agent is a polyclonal antibody.

12. The method of claim 9, wherein the detection agent is a monoclonal antibody.

13. The method of claim 9, wherein the detection agent is a polyclonal antibody.

14. The diagnostic method of claim 8 or 9, further comprising removing fibrinogen from the sample.

15. The diagnostic method of claim 8 or 9, wherein the thrombotic or thromboembolic disease is a deep venous thrombosis (DVT) or a pulmonary embolism (PE).

16. The method of claim 8 or 9, wherein a concentration of FPB and/or des-arginine FPB peptides in the sample above 50 ng/ml is reported as indicative of thrombotic or thromboembolic disease.

17. The method of claim 8 or 9, wherein a concentration of FPB and/or des-arginine FPB peptides in the sample above 100 ng/ml is reported as indicative of thrombotic or thromboembolic disease.

18. The method of claim 8 or 9, wherein the detection agent is an Fab, F(ab)$_2$, or Fv antibody fragment.

19. The method of claim 8 or 9, wherein the detection agent is attached to a substrate.

20. The method of claim 19, wherein the substrate is a gel, hydrogel, resin, bead, nitrocellulose, nylon filter, microtiter plate, culture flask, or polymeric material.

21. The method of claim 8 or 9, wherein the detection agent further comprises a detectable moiety.

22. The method of claim 21, wherein the detectable moiety is a radionuclide, enzyme, specific binding pair component, colloidal dye substance, fluorochrome, reducing substance, chemiluminescent substance, electrochemiluminescent substance, electroactive substance, latex, digoxigenin, metal, particulate, dansyl lysine, antibody, protein A, protein G, electron dense material, or chromophore.

23. The method according to claim 8 or 9, wherein the detection step (b) is by enzyme-linked immunosorbent assay, immunonephelometry, agglutination, precipitation, immunodiffusion, immunoelectrophoresis, immunofluorescence, electrochemiluminescence, surface plasmon resonance, chemiluminescence, electrochemical immunoassay, radioimmunoassay, or immunohistochemistry.

* * * * *

UNITED STATES PATENT AND TRADEMARK OFFICE
CERTIFICATE OF CORRECTION

PATENT NO. : 6,673,561 B1
DATED : January 6, 2004
INVENTOR(S) : Morris

It is certified that error appears in the above-identified patent and that said Letters Patent is hereby corrected as shown below:

<u>Title page,</u>
Item [56], References Cited, OTHER PUBLICATIONS, "Owens, R.J. et al." reference, delete "engineeringof" and insert -- engineering of --, therefor.

<u>Column 39,</u>
Line 15, delete "(FFB)" and insert -- (FPB) -- , therefor.

Signed and Sealed this

First Day of June, 2004

JON W. DUDAS
*Acting Director of the United States Patent and Trademark Office*

SEQUENCE LISTING

```
<160> NUMBER OF SEQ ID NOS:  6

<210> SEQ ID NO 1
<211> LENGTH: 15
<212> TYPE: PRT
<213> ORGANISM: Artificial Sequence
<220> FEATURE:
<223> OTHER INFORMATION: Cys-FPB

<400> SEQUENCE: 1

Cys Gln Gly Val Asn Asp Asn Glu Glu Gly Phe Phe Ser Ala Arg
 1               5                  10                  15

<210> SEQ ID NO 2
<211> LENGTH: 14
<212> TYPE: PRT
<213> ORGANISM: Artificial Sequence
<220> FEATURE:
<223> OTHER INFORMATION: Cys-desArg-FPB

<400> SEQUENCE: 2
```

-continued

```
Cys Gln Gly Val Asn Asp Asn Glu Glu Gly Phe Phe Ser Ala
 1               5                  10

<210> SEQ ID NO 3
<211> LENGTH: 14
<212> TYPE: PRT
<213> ORGANISM: Homo sapiens

<400> SEQUENCE: 3

Gln Gly Val Asn Asp Asn Glu Glu Gly Phe Phe Ser Ala Arg
 1               5                  10

<210> SEQ ID NO 4
<211> LENGTH: 13
<212> TYPE: PRT
<213> ORGANISM: Homo sapiens

<400> SEQUENCE: 4

Gln Gly Val Asn Asp Asn Glu Glu Gly Phe Phe Ser Ala
 1               5                  10

<210> SEQ ID NO 5
<211> LENGTH: 14
<212> TYPE: PRT
<213> ORGANISM: Homo sapiens
<220> FEATURE:
<221> NAME/KEY: SITE
<222> LOCATION: 1
<223> OTHER INFORMATION: Xaa = pyroglutamic acid

<400> SEQUENCE: 5

Xaa Gly Val Asn Asp Asn Glu Glu Gly Phe Phe Ser Ala Arg
 1               5                  10

<210> SEQ ID NO 6
<211> LENGTH: 13
<212> TYPE: PRT
<213> ORGANISM: Homo sapiens
<220> FEATURE:
<221> NAME/KEY: SITE
<222> LOCATION: 1
<223> OTHER INFORMATION: Xaa = pyroglutamic acid

<400> SEQUENCE: 6

Xaa Gly Val Asn Asp Asn Glu Glu Gly Phe Phe Ser Ala
 1               5                  10
```